US010383894B2

(12) United States Patent
Tran et al.

(10) Patent No.: US 10,383,894 B2
(45) Date of Patent: Aug. 20, 2019

(54) HUMAN MEDICINAL TREATMENT USING SALT OF PEROXYMONOSULFURIC ACID

(75) Inventors: David Van Tran, San Jose, CA (US); David Nguyen Tran, San Jose, CA (US)

(73) Assignee: LuTran Industries, Inc., San Jose, CA (US)

( * ) Notice: Subject to any disclaimer, the term of this patent is extended or adjusted under 35 U.S.C. 154(b) by 1321 days.

(21) Appl. No.: 12/726,326

(22) Filed: Mar. 17, 2010

(65) Prior Publication Data

US 2011/0229583 A1   Sep. 22, 2011

(51) Int. Cl.
*A61K 33/40* (2006.01)
*A61K 31/185* (2006.01)

(52) U.S. Cl.
CPC ............ *A61K 33/40* (2013.01); *A61K 31/185* (2013.01)

(58) Field of Classification Search
None
See application file for complete search history.

(56) References Cited

U.S. PATENT DOCUMENTS

| | | |
|---|---|---|
| 2,091,167 A | 8/1937 | Solley |
| 2,159,986 A | 5/1939 | Gray et al. |
| 3,873,696 A | 3/1975 | Randeri et al. |
| 4,404,191 A | 9/1983 | Sporkenbach et al. |
| 4,822,512 A | 4/1989 | Auchincloss |
| 5,106,879 A | 4/1992 | Clark |
| 5,135,952 A * | 8/1992 | Ohmori et al. ............... 514/547 |
| 5,139,763 A | 8/1992 | Amini |
| 5,186,946 A | 2/1993 | Valliéres |
| 5,234,914 A * | 8/1993 | Gallina ........................ 514/54 |
| 5,308,838 A | 5/1994 | McAnalley |
| 5,344,829 A | 9/1994 | Chiou |
| RE35,152 E | 2/1996 | Rubin et al. |
| 5,595,997 A | 1/1997 | Aberg et al. |
| 5,935,579 A | 8/1999 | Habeshaw et al. |
| 6,066,333 A | 5/2000 | Willis et al. |
| 6,130,338 A | 10/2000 | Muraoka et al. |
| 6,342,537 B1 | 1/2002 | Thomsen et al. |
| 6,346,537 B1 | 2/2002 | Hata et al. |
| 6,555,020 B1 | 4/2003 | Chadwick et al. |
| 6,723,713 B2 | 4/2004 | Sequeira et al. |
| 6,849,624 B2 | 1/2005 | Ballard et al. |
| 7,090,820 B2 | 8/2006 | Martin |
| 7,119,091 B2 | 10/2006 | Habashita et al. |
| 7,442,323 B2 | 10/2008 | Durante et al. |
| 7,560,033 B2 | 7/2009 | Lightcap et al. |
| 2003/0091644 A1* | 5/2003 | Bologna et al. ............... 424/486 |
| 2003/0113349 A1* | 6/2003 | Coleman, III ............... 424/239.1 |
| 2003/0232086 A1* | 12/2003 | McCadden ............ A61K 31/56 424/486 |
| 2004/0059110 A1 | 3/2004 | Nakano et al. |
| 2005/0062017 A1 | 3/2005 | Martin |
| 2007/0244195 A1* | 10/2007 | Burkhart et al. ............. 514/568 |
| 2010/0021530 A1 | 1/2010 | Weinfield |

OTHER PUBLICATIONS

Staumont-Salle et al. "Etiological diagnosis and treatment of chronic urticaria" Rev Med Interne (2003) vol. 24, No. 1, pp. 34-44.*
Shiel, William C., Jr., "Osteoarthritis" emidicinehealth [online], retrieved from the internet on (Apr. 22, 2013) from URL <http://www.emedicinehealth.com/osteoarthritis/page11_em.htm> (Nov. 18, 2006).*
Virkon S websites, (2000), accessed Nov. 14, 2013 from URL<http://web.archive.org/web/20000304132626/http://www.antecint.co.uk/main/virkons.htm> and from following the hyperlinks on this page.*
Virkon S MSDS, (2012), accessed Nov. 14, 2013 from URL <http://www.pharmacal.com/MSDS/US/MSDSVirkonSUseDilution.pdf>.*
Misra, Mahesh C. "Drug treatment of haemorrhoids." Drugs 65.11 (2005): 1481-1491.*
Baeten, Jared M., et al. "Antiretroviral prophylaxis for HIV prevention in heterosexual men and women." New England Journal of Medicine 367.5 (2012): 399-410.*
Brożek, Jan L., et al. "Allergic Rhinitis and its Impact on Asthma (ARIA) guidelines: 2010 revision." Journal of Allergy and Clinical Immunology 126.3 (2010): 466-476.*
Okeson, JP. "Non-odontogenic toothache." Northwest Dentistry 79.5 (2000): 37-44.*
Banerjee, Dibyajyoti, and Deepak Kaul. "Combined inhalational and oral supplementation of ascorbic acid may prevent influenza pandemic emergency: A hypothesis." Nutrition 26.1 (2010): 128-132.*
Weinstein, Andrew, and Brian Berman. "Topical treatment of common superficial tinea infections." American family physician 65.10 (2002).*
"Virusnip Farm Disinfectant", Novartis Animal Health, 2006, 6 pp.
Alegente et al., "The Sterilizing Activity of Virkon on Microorganisms Isolated From Eye Infections and on Surgical Instruments Used in Ocular Surgery", Lab. of Microbiology, Hospital S.Maria della Scala, Siena Ophthalmology Dept., università degli Studi di Siena, undated, seemingly prior to 2003, 13 pp.
Anipsitakis et al., "Heterogeneous Activation of Oxone Using Co3O4", abstract, J. Phys. Chem. B, 2005, 1 p., full paper, pp. 13052-13055.
Anipsitakis, "Cobalt/Peroxymonosulfate and Related Oxidizing Reagents for Water Treatment", Abstract and Extended Summary, Ph.D. thesis, Univ. of Cincinnati, 2005, pp. ii-iv and vi-ix.
Ares-Mazás et al., "Effect of a commercial disinfectant ('Virkon') on mouse experimental infection by Cryptosporidium parvum", *J. Hosp Infect.*, Jun. 1997, pp. 141-145.
Green, "Oxygenation Therapy: Unproven Treatments for Cancer and AIDS", *Sci. Rev. Alternative Medicine*, Spring/Summer 1998, 9 pp.
Patnayak et al., "Efficacy of Disinfectants and Hand Sanitizers Against Avian Respiratory Viruses", *Avian Diseases*, Jun. 2008, pp. 199-202.

(Continued)

*Primary Examiner* — Sue X Liu
*Assistant Examiner* — Daniel L Branson
(74) *Attorney, Agent, or Firm* — Ronald J. Meetin

(57) ABSTRACT

A medicinal drug is administered to a person for treating allergic rhinitis, hemorrhoids, toothache, bromhidrosis, or urticaria. The medicinal drug is formed at least partially with salt of peroxymonosulfuric acid, preferably potassium hydrogen peroxymonosulfate.

64 Claims, No Drawings

(56) References Cited

OTHER PUBLICATIONS

Rivas, "Catalytic Decomposition of Potassium Monopersulfate. Influence of Variables", *World Acad. Sci., Engrg. and Tech.*, vol. 57, 2009, pp. 218-222.

Shelton, The Ringworm Battle Plan, www.pandecats.com/x/ringworm_battle_plan.shtml, Jan. 2002, 5 pp.

Steele, "The standard enthalpy of formation of peroxymonosulfate ($HSO_5^-$) and the standard electrode potential of the peroxymonosulfate-bisulfate couple", abstract, *J. Chem. Thermodyn.*, Apr. 1982, 1 p., full paper, pp. 337-344.

"A summary of the Viral efficacy of Antec Virkon", Antec International, Jun. 27, 2003, 3 pp.

"DuPont Material Safety Data Sheet, Oxone SCG72", DuPont, Jun. 6, 2007, pp. 1-8.

"DuPont Oxone Monopersulfate Compound, General Technical Attributes", E.I. du Pont de Nemours and Co., 2008, 4 pp.

"Oxone, Potassium peroxomonosulfate", www.organic-chemistry.org/chemicals/oxidations/oxone-potassiumperoxomonosulfate.shtm, circa 2008, 5 pp.

"Pet Virkon", peticious.com/virkon-500g-makes-50litre--add-water-to-make-disinfectant.html, 2008-2010, 1 p.

"Tackling ringworm in cats", Feline Advisory Bureau, www.fabcats.org/owners/skin/www.fabcats.org, Nov. 2008, 6 pp.

"Virkon Aquatic", brochure, Aquatic Life Sciences, circa 2008, 8 pp.

"Virkon Aquatic", label, Aquatic Life Sciences, circa 2008, 2 pp.

"Virkon Aquatic—Directions for General Use", Aquatic Life Sciences, circa 2008, 1 p.

"Virkon Aquatic—Mode of Action", Aquatic Life Sciences, circa 2008, 2 pp.

"Virkon Disinfectant/Cleaner P.W.S.", label, Vétoquinol Canada, circa 2008, 4 pp.

"Virkon S", E.I. du Pont de Nemours and Co., Jan. 2010, 2 pp.

"Virkon S Bacterial Activity", Antec International, May 8, 2003, 7 pp.

"Virkon S Broad Spectrum Disinfectant", master label, Antec International, Mar. 12, 2003, 11 pp.

"Virkon S Disinfectant and Virucide", E.I. du Pont de Nemours and Co., 2009, 2 pp.

"Virkon S Fungicidal Activity", Antec International, Jan. 17, 2001, 5 pp.

"Virkon S Horticultural Efficacy Data", Antec International, Jul. 19, 2003, 2 pp.

"Virkon S Safety Data Sheet HSD/36G", Antec International, Jan. 10, 2008, 6 pp.

"Virkon S Sporicidal Activity", Antec International, circa 2003, 1 p.

"Virkon S Tablets", E.I. du Pont de Nemours and Co., Jan. 2010, 3 pp.

"Virkon S Virucidal Activity", Antec International, May 20, 2002, 6 pp.

"Virusnip Farm Disinfectant", Novaritis Animal Health, 2006, 6 pp.

"We are selling all the basic koi medicine online, covering all possible ailments", www.koionline.co.za/medication.htm, undated, 2 pp, 2008.

* cited by examiner

HUMAN MEDICINAL TREATMENT USING SALT OF PEROXYMONOSULFURIC ACID

CROSS-REFERENCE TO RELATED APPLICATION

This claims priority to U.S. provisional patent application 61/161,991, filed 20 Mar. 2009, the contents of which are incorporated by reference to the extent not repeated herein.

FIELD OF USE

This relates to the treatment of humans using medicinal drugs.

BACKGROUND OF THE INVENTION

Inflammation is caused by tissue injury consisting of complex reactions involving vascular and connective tissues. Tissue damage may result from microbial invasion, auto-immune processes, tissue infection, allograft rejection, and such hurtful and/or destructive external influences as heat, cold, radiant energy, electrical or chemical stimuli, and mechanical trauma. Tissue damage may involve any part of the human body such as the joints (arthritis), bowels (inflammatory bowel disease), and lungs (pulmonary inflammation). Whatever the cause or bodily site, inflammatory responses to tissue damage are quite similar, consisting of complicated functional and cellular adjustments involving microcirculation, fluid shifts, and inflammatory cells (leukocytes). When tissue damage occurs, soluble chemical substances are elaborated which initiate the inflammatory response. Inflammation can be mild and self-limited or prolonged and seriously debilitating and chronic.

Numerous drugs have been developed to fight inflammation in humans. The most prominent in current treatment are anti-inflammatory steroidal drugs, corticosteroids and non-steroidal anti-inflammatory drugs ("NSAIDs") such as salicylates. While these drugs are generally effective, they often have adverse side effects.

Corticosteroids are powerful anti-inflammatory drugs that suppress both acute and chronic phases of inflammation. Unfortunately, corticosteroids also suppress the immune response and sometimes decrease certain essential cell repair processes. Use of excessive doses or/and long term use of corticosteroids may lead to hypercorticism or/and suppression of hypothalamic-pituitary-adrenal function. Corticosteroids must generally be given by injection and are not effective via oral administration.

A topically active corticosteroid may be effective in treating bronchial asthma. While topically active corticosteroids administered by metered-dose inhalation have greatly reduced some adverse side effects of steroid therapy in treating bronchial asthma, a large portion of an inhaled corticosteroid dose is swallowed by the patient. The swallowed portion may reach the systemic circulation through the gastrointestinal tract and cause adverse systemic side effects including high blood pressure, cataracts, glaucoma, and worsening of diabetes. Intranasal corticosteroids should be used with caution, if at all, in patients with active or quiescent tuberculosis infections of the respiratory tract, untreated local or systemic fungal or bacterial infections, systemic viral or parasitic infections, or/and herpes simplex.

NSAIDs such as salicylates, phenylbutazone, indomethacin, ibuprofen, and naproxen have been tried in order to avoid adverse side effects in the treatment of uveitis. The results have generally not been satisfactory. Furthermore, NSAIDs commonly affect the gastrointestinal tract, the liver, kidney, spleen, blood, and bone marrow and produce adverse side effects such as edema, nausea, stomatitis, epigastric pain, and drug rash. NSAIDs are typically not effective in treatment of some chronic inflammatory disorders including asthma and lower back pain.

A pathogen is an infectious biological agent, sometimes referred to as a germ, which causes disease or illness to its host. Many medical advances, such as vaccination, antibiotics, and fungicides, have been used to safeguard against infection by pathogens. Nevertheless, pathogens continue to threaten human life. Primary pathogens are bacteria, eukaryotes, prions, and viruses.

Bacteria constitute one of the smallest organisms containing all the material required for growth and self-replication. A bacterium has a rigid cell wall surrounding a cytoplasmic membrane that encloses a single naked chromosome without a nuclear membrane. The cytoplasmic membrane consists primarily of a bilayer of lipid molecules.

Bacterial pathogens cause infectious diseases such as tuberculosis, cholera, and syphilis. The most common fatal bacterial diseases are respiratory infections. Some bacterial pathogens, such as staphylococcus, can cause skin infections, meningitis, pneumonia, and even overwhelming sepsis, a systemic inflammatory response producing shock, massive vasodilation, and death. Opportunistic bacterial pathogens cause disease mainly in patients suffering from immunosuppression or cystic fibrosis.

Bacterial infections can be treated with antibiotics, classified as bacteriocidal if they kill bacteria and as bacteriostatic if they prevent the bacteria from multiplying so the human immune system can overcome them. There are many types of antibiotics. Each type of antibiotic inhibits a process whose pathogen is different from that found in the host. The effectiveness of individual antibiotics varies with the location of the infection, the ability of the antibiotic to reach the site of infection, and the ability of the bacteria to resist or inactivate the antibiotic.

The adverse side effects of antibiotics are varied, and range from fever and nausea to major allergic reactions. One of the more common adverse side effects is diarrhea, sometimes caused by the anaerobic bacterium clostridium difficile, which results from the antibiotic disrupting the normal balance of intestinal flora. Other adverse side effects may result from interaction with other drugs, such as elevated risk of tendon damage from administration of a guinolone antibiotic with a systemic corticosteroid.

Antibiotics are among the drugs commonly misused by physicians. For instance, antibiotics are often misapplied for combating viral respiratory tract infections. Widespread and injudicious use of antibiotics has led to the emergence of antibiotic-resistant pathogens. This poses a serious threat to public health. The antibiotic-resistance problem raises a need for increased efforts to seek antibacterial agents effective against pathogenic bacteria resistant to current antibiotics.

Fungi are eukaryotic pathogens similar to bacteria. One of the differences is that fungal nucleic acid, consisting of multiple chromosomes, is enveloped by a nuclear membrane. In some fungi (as in some bacteria), the cell wall is surrounded by an external capsular polysaccharide which, in at least the case of bacteria, protects the pathogenic microbe from phagocytosis and thereby plays a major role in determining virulence.

Fungi are responsible for numerous diseases such as *aspergillosis,* psoriasis, *aspergilloma,* and dandruff. Symptoms of *aspergillosis* include hemoptysis (coughing up blood), blood clots, chest pain, delirium, and fever. Persons severely infected with *aspergillosis* may also develop kidney and liver failure. Voriconazole is commonly used to treat *aspergillosis*. However, a large percentage of persons treated with voriconazole report visual disturbances that generally occur thirty minutes after administration and last for about thirty more minutes. Consequently driving or risky tasks should be avoided. Other common adverse side effects associated with voriconazole include fever, nausea, rash, overwhelming sepsis, and respiratory disorders. Corticosteroids which have the above-mentioned adverse side effects can be used to treat allergic bronchopulmonary *aspergillosis*.

Symptoms of psoriasis include red patches covered with silvery scales of the skin, dry cracked skin that can bleed, burning, itching, pain, disfiguring nails, and swollen and stiff joints. Psoriasis is commonly treated with corticosteroids. While corticosteroids can be effective, they have the above-mentioned adverse side effects, including a risk of suppressing the immune response and a decrease in many aspects of essential cell repair processes. Corticosteroids often irritate normal skin, cannot be used for long periods of time, and have an unpleasant odor. Additionally, abrupt withdrawal of corticosteroids can cause an aggressive recurrence of the condition.

Individuals infected with *aspergilloma,* a serious lung disease, commonly do not have significant readily noticeable symptoms. An *aspergilloma* infestation may be present for years until it is diagnosed sometimes due to coughing up blood. Medications to treat *aspergilloma* have not been shown to eradicate the fungi. Surgery can be used to treat *aspergilloma* and is often the only choice to control bleeding in life-threatening situations. *Aspergilloma* surgery generally has a high risk of major complications including changes in local blood flow, hemorrhage, inflammation, infection, loss of function, and scarring. Conventional dandruff treatments are discussed below.

Spores are metabolic byproducts of the life cycle of some bacteria and fungi. Bacteria produce endospores located within the cytoplasm of the parental cells. Bacterial spores may occur when food is uncooked. This can cause foodborne illnesses such as heavy nausea, vomiting, and abdominal periods.

Fungi produce a variety of exospores, including *aspergillus* spores and conidia spores. If large amounts of *aspergillus* spores are inhaled, *aspergillosis* may occur. *Aspergillus* spores are one of the most common causes of fungal ear infections which can cause pain, temporary hearing loss and, in severe cases, damage to the ear canal and tympanic membrane. Conidia spores are non-motile fungal spores present in the air. An average person inhales 40 conidia per hour. Conidia often leads to immunocompromise, i.e., the immune system is not strong enough to fight off the fungi as the lungs are colonized, resulting in pulmonary infection.

Spores are highly resistant to physical and chemical agents. Research is ongoing to find safe and effective treatments for debilitating conditions produced by spore pathogens.

In medical parasitology, the term "parasite" means a eukaryotic pathogenic organism. Hence, protozoan and metazoan infectious agents are classified as parasites whereas bacteria and viruses are not. Many parasites, such as protozoa, fleas, and worms (helminths), carry disease or cause sores or lesions which can become infected. Protozoan parasites that can cause human disease include amoeba entamoeba histolytica, the cause of amoebic dysentery and liver abscess as further discussed below.

Parasites live on or in their hosts from which the parasites get some or all of their nourishment. Although parasites are generally harmful to their hosts, the damage ranges widely from minor inconvenience to debilitating or fatal disease. An ectoparasite, such as a louse, tick, or leech, lives or feeds on the outer surface of the host's body. Ectoparasites do not usually cause disease themselves. However, they are frequently a vector of disease. For example, tick parasites transmit organisms that can cause diseases such as Lyme disease as discussed below. An endoparasite lives inside the body of its host. Endoparasites include organisms such as tapeworms, hookworms, and *trypanosomes* that live within the host's organs or tissues as well as organisms such as sporozoans that invade the host's cells. Endoparasites commonly cause malaria as discussed below. Many parasites have extremely specialized reproductive systems and complex life cycles involving more than one host.

Amoebiasis, an infection caused by the protozoan parasite amoeba entamoeba histolytica, is contracted by ingesting water or food contaminated with amoebic cysts. Symptoms of amoebiasis include mild diarrhea to severe dysentery (diarrhea with blood and mucus), and liver abscess. Metronidazole is used to destroy amoebae that have invaded tissue. However, metronidazole produces adverse side effects such as nausea, diarrhea, and metallic taste. High doses and/or long-term systemic treatment with metronidazole is associated with the development of furry black tongue, leukopenia, neutropenia, increased risk of peripheral neuropathy, and central nervous system toxicity. The International Agency for Research on Cancer lists metronidazole as a potential human carcinogen.

Lyme disease is primarily caused by the bacterium borrelia and is contracted through the bite of infected ixodes ticks. Symptoms of Lyme disease include fatigue, fever, malaise, muscle pain and soreness, and erythema migrans (circular rash). Persons diagnosed with Lyme disease need to be treated immediately to avoid systemic complications in the central nervous system and heart. Lyme disease is typically treated with antibiotics such as doxycycline which can be effective. The adverse side effects of antibiotics are discussed above.

Malaria, a vector-borne infectious disease widespread in tropical and subtropical regions, is caused by the parasitic protozoa plasmodium. Symptoms of malaria include anemia, arthralgia, convulsions, fever, retinal damage, headache, hemoglobinuria, shivering, and vomiting. Other symptoms include hepatomegaly, hypoglycemia, hemoglobinuria with renal failure, splenomegaly, brain damage, and coma sometimes leading to death. No vaccine is currently available for malaria. Malarial infections are treated with anti-malarial drugs such as chloroquine or pyrimethamine. Drug resistance is increasingly common, especially for chloroquine. Pyrimethamine may deplete folic acid resulting in hematologic side effects and hypersensitivity reactions, leukopenia, and hematuria. When used with a sulfonamide, pyrimethamine may also cause atrophic glossitis, cardiac arrhythmias, megaloblastic anemia, and hyperphenylalaninemia.

A prion is an infectious agent generally made solely of protein and lacking nucleic acid. Prions are believed to infect and propagate by refolding abnormally into a structure which converts normal molecules of the protein into an abnormally structured form. More particularly, all known prions are believed to infect and propagate by forming an amyloid fold in which the protein polymerizes into a fiber with a core consisting of tightly packed beta sheets. It is often assumed that the diseased form directly interacts with the normal form to make it rearrange its structure. This converted structure is stable and accumulates, causing tissue damage and cell death.

Prion infectious diseases include transmissible spongiform encephalopathic diseases such as Creutzfeldt-Jakob disease, Gerstmann-Sträussler-Scheinker syndrome, fatal familial insomnia, and kuru. Alpers' syndrome may also be a cause of prion diseases. All of these prion-caused diseases affect the structure of the brain or other neural tissue and are fatal. Prions are generally quite resistant to denaturation by protease, heat, radiation, and formalin treatments, although potency or infectivity may be reduced. Ozone sterilization has shown some effectiveness in treating prion infectious diseases.

A virus consists of a single nucleic acid, either deoxyribonucleic acid ("DNA") or ribonucleic acid ("RNA"), and a protein shell or coat surrounding the nucleic acid. A complete viral particle is called a virion. Some viruses contain lipids and carbohydrates. Virions lack constituents fundamental for growth and multiplication, i.e., they never "grow". Virions are by themselves metabolically inert. Virions replicate only after cell-host invasion, and therefore are obligatory intracellular parasites. Hence, a virus is more than a simple nucleoprotein (a chemical substance), but not quite a microbe (a living entity). In other words, a virus is slightly short of the threshold of life as commonly defined.

A virus uses the machinery of a host cell to reproduce and resides within the host cell. Consequently, viruses are difficult to eliminate without killing the host cells. It is believed that viral infections trigger inflammatory responses which do not respond to anti-viral drugs.

Patients often ask for, and physicians often prescribe, antibiotics. While antibiotics destroy or prevent the growth of bacteria, antibiotics are useless in treating viral (and fungal) infections. Their misuse in treating viral diseases is one of the causes of antibiotic resistance to bacteria. Nevertheless, the prudent course of action in life-threatening situations is to begin antibiotic treatment while waiting for test results to determine whether a person's symptoms are caused by a viral or bacterial infection.

The alternative to drug treatment is a vaccine to prevent infection. Vaccines can be active or passive. An active vaccine causes the body to produce antibodies that create an "immune response" against an attacking organism. A passive vaccine generally consists of pre-produced antibodies, e.g., from a mouse, rabbit or monoclonal antibody-producing cell line, which recognizes and attacks the virus, without the person's body doing anything. That is, the body does not have to produce an immune response.

There are various ways to provide vaccination against a viral disease. One way is to inject a person with a preparation of killed or seriously weakened (attenuated) virus. The problem with this approach is that a catastrophic may result if, for some reason, the virus "catches" and the person actually contracts the viral disease.

The injection approach has been investigated for treating acquired immune deficiency syndrome ("AIDS") caused by human immunodeficiency virus ("HIV") but with limited success. The resultant immunity is typically sufficient to provide protection against individual isolates of HIV, but not to HIV from any source. This is primarily because the coat proteins on the surface of the HIV particles are inherently variable and can even vary from one infected person to another. The vaccination injection approach is thus unsatisfactory because the person is at risk for catching AIDS and because the vaccine does not guarantee protection.

More generally, vaccines do not guarantee complete protection from many diseases, particularly viral diseases. Even after vaccination against a particular disease, a vaccinated person may still get the disease due to the host's immune system not responding adequately or at all. This may be due to a lowered immunity in general resulting, for example, from diabetes, steroid use, or HIV infection or the person's immune system lacking B-cells capable of generating the requisite antibodies.

Additionally, the strain of a disease contracted by a person may be different than the strain vaccinated against. In this regard, some viruses such as common cold and influenza viruses can mutate and are highly efficient at mutating. The mutated form of the virus may be so different from the form vaccinated against that the immune system is unable to defeat the infection. The disease is, however, often at a milder level in a person vaccinated against the disease.

Hepatitis is an inflammation of the liver characterized by the latency of inflammatory cells in the tissue of the liver. A virus usually causes hepatitis. The most common viral strains are Hepatitis A, Hepatitis B, Hepatitis C, Hepatitis D, and Hepatitis E. Hepatitis can also arise from non-viral sources such as autoimmune conditions (systemic lupus erythematosus), metabolic diseases (Wilson's disease), hereditary factors, primary biliary cirrhosis, toxins, and drugs (paracetamol and amoxycillin). A notable toxic cause of hepatitis is alcohol. The combination of hepatitis C and alcohol consumption accelerates the development of cirrhosis, i.e., scarring of the liver.

Some people with viral hepatitis have no signs of the infection. Viral hepatitis can be self-limited and thus go away on its own. For other people, symptoms of fever, vomiting, diarrhea, dark-colored urine and pale bowel movements, jaundice, and profound loss of appetite can occur. When chronic or life-long infection of hepatitis ensues, the liver swells and damage occurs. In addition to cirrhosis, this can lead to liver failure and liver cancer.

Hepatitis A can be prevented by vaccination with a high success rate. A hepatitis A vaccine contains inactivated hepatitis A virus that provides active immunity against future infection. If a booster vaccination is given six to twelve months after the initial vaccination, protection against hepatitis A can last upwards of 20 years. Common adverse side effects of Hepatitis A vaccination are drowsiness, loss of appetite, and fever. Caution must be taken if a previous dose of any hepatitis A-containing vaccine, including neomycin (aminoglycoside antibiotic) has been injected because this can lead to a severe allergic reaction (anaphylaxis). There is currently no specific treatment for hepatitis A.

Several vaccines are available for preventing hepatitis B. These vaccines rely on the use of one of the viral envelope proteins (hepatitis B surface antigen). The success rate is high, and immunity can last over 20 years. Infants can be vaccinated at birth. Available antiviral drugs, such as lamivudine, adefovir, tenofovir, telbivudine, entecavir and immune system modulators interferon alpha-2a, and PEGylated interferon alpha-2a, can stop the hepatitis B virus from replicating and thereby minimize liver damage. However, they cannot clear a hepatitis B infection. A liver transplant for end-stage chronic hepatitis B may be effective in overcoming the disease. Adverse side effects of liver transplantation include bleeding, infection, painful incision, possibility of blood clots, prolonged recovery, and death.

Hepatitis C produces chronic infection in 50-80% of infected people. Approximately 50% of chronically infected people do not respond to therapy. Current treatment techniques for hepatitis C include a combination of pegylated interferon-alpha-2a or pegylated interferon-alpha-2b and ribavirin for 24 or 48 weeks. If at least a 2-log viral load reduction does not occur after 12 weeks of treatment, the success rate in overcoming hepatitis C is less than 1%. Also, the treatment can be mentally and physically demanding and can sometimes cause temporary disability. A substantial fraction of treated persons experience adverse side effects ranging from flu-like symptoms to severe adverse effects such as anemia and cardiovascular complications. Due to the physiological rigors of the treatment, some infected people may attempt or consider suicide.

There are currently no successful treatments for chronic hepatitis D. In combination with the hepatitis B virus, hepatitis D has the highest mortality rate of all hepatitis infections.

Many people with hepatitis E experience a self-limited illness and go on to recover completely. However, there is currently no therapy or medicine effective against chronic hepatitis E. In many cases, hospitalization is recommended for the severely ill. Supportive care may be needed.

Herpesviruses or herpesviridae is a family of eight DNA viruses. The members of the family are herpes simplex virus 1 ("HSV-1"), herpes simplex virus 2 ("HSV-2"), varicella zoster virus (chicken pox and shingles), Epstein-Barr virus (infectious mononucleosis, Burkitt's lymphoma, central nervous system lymphoma in AIDS patients, post-transplant lymphoproliferative syndrome, nasopharyngeal carcinoma, and HIV-associated hairy leukoplakia), cytomegalovirus (infectious mononucleosis-like syndrome and retinitis), two roseoloviruses (roseola infantum and exanthem subitum), and Kaposi's sarcoma-associated herpes rhadinovirus (primary effusion lymphoma and types of multicentric Castleman's disease implicated as a cause of cancer in people with AIDS).

Herpes simplex infections, generally referred to as herpes simplex 1 and herpes simplex 2, are primarily oral and genital. They generally occur when HSV-1 or HSV-2 comes into contact with the oral mucosal tissue, abraded skin of the mouth, the face, or the genital area. Herpes simplex 1, predominantly orofacial, is usually acquired orally during childhood but may be sexually acquired. Herpes simplex 2, predominantly genital, is sexually transmitted in most cases. Herpes simplex 1 tends to be more common than herpes simplex 2. However, cases of oral infection by HSV-2 are increasing.

Herpes labialis, often referred to as cold sores, is a common type of herpes infection caused by HSV-1 or HSV-2. Cold sores, whether initial or recurring, are usually first felt as a tingling or itching sensation in the affected location. The initial feelings are normally followed, depending on the severity of the infection, by the emergence of a raised or swollen area on the skin. The blister or swollen area becomes generally painful but acutely sore when touched, stretched, or moved. In a few days to a few weeks, the sore area abscesses and emits a virus-laden clear fluid for several days before scabbing over. Once scabbed over, the lesion usually heals completely in a week to ten days. In immune-compromised people, this cycle may be significantly extended.

There is currently no cure or treatment to eradicate herpes simplex 1 or 2 from the body at activations of HSV-1 or HSV-2. An analgesic such as paracetamol can reduce pain and fever during outbreaks of herpes simplex 1 or 2 but has adverse side effects including hemolytic anemia, jaundice, leukopenia, neutropenia, pancytopenia, and thrombocytopenia. In addition, high-dose usage of paracetamol increases the risk of gastrointestinal complications such as stomach bleeding.

Topical docosanol, an antiviral agent, is used to treat the symptoms of HSV-1 and HSV-2 infections around the mouth. Docosanol may help relieve pain and moderately reduce the healing time (if any) of cold sores. There are conflicting reports on the efficacy of topical docosanol in actually helping herpes simplex infections to heal faster. A common adverse side effect of docosanol is headache.

There is currently no cure for any of the other six herpes viral infections. The herpes infection remains within its host cell in a dormant state and can reactivate at anytime to produce further conditions of the disease.

Herpes infections are typically treated with antiviral drugs, such as docosanol, that intervene with viral replication by providing an immune response, alleviating duration, frequency, and severity, and reducing chance of transmission to others. Other antiviral drugs for treating some herpes infections include acyclovir, ganciclovir, and valacyclovir. Acyclovir has low water solubility and therefore poor oral bioavailability, making intravenous administration necessary at high concentrations. Adverse side effects associated with systemic acyclovir include nausea, vomiting, diarrhea, headache, and, in large doses, hallucinations. Valaciclovir is a prodrug, an esterified version of acyclovir that has greater oral bioavailability than acyclovir. Valaciclovir has adverse side effects similar to those of acyclovir. Ganciclovir is correlated to a range of serious hematological adverse effects. The common adverse side effects of ganciclovir are anemia, fever, dyspepsia, anorexia, and seizures. Ganciclovir is considered a potential human carcinogen, mutagen, and teratogen.

The efforts of researchers in developing treatments for viral infections have been repeatedly frustrated by both the morphology and the metabolic nature of viruses. In brief, no efficient way for treating many viral diseases is currently available. There is a critical need for treatments which are effective and safe and display minimal adverse side effects.

An allergy is an abnormal, acquired sensitivity to a given substance, including pollen, drugs, or numerous environmental triggers through a local or systemic inflammatory response. Allergies are characterized by sneezing, runny nose, and itchy eyes. Allergic rhinitis, commonly known as "hay fever", is an allergy particularly prevalent from late May to the end of June.

Antihistamines may relieve the symptoms of allergic rhinitis but can cause drowsiness. Corticosteroid nasal sprays such as fluticasone and mometasone furoate can be effective but have adverse side effects. See U.S. Pat. No. 6,723,713 B2 with regard to mometasone furoate.

Arthritis is a group of over 100 medical conditions involving damage to the joints of the body. Osteoarthritis (degenerative joint disease), the most common form of arthritis, is variously caused by trauma to a joint, infection of the joint, or aging. In osteoarthritis, wearing of the cartilage that covers and acts as a cushion inside the joint produces low-grade inflammation that results in pain in the joint. As the bone surfaces become less well protected by cartilage, joint pain is experienced during weight bearing, walking, and standing. Symptoms of osteoarthritis include acute pain in the bones and muscles, particularly neck and back pain, burning sensations in the associated muscles and tendons, swelling, tenderness, and muscle spasms.

Osteoarthritis is generally treated with NSAIDs and local injections of glucocorticoids. NSAIDs have the adverse side effects discussed above and further below. Glucocorticoids have the adverse side effects discussed below. In severe cases, joint replacement surgery is performed to alleviate osteoarthritis. Regeneration of cartilage has not yet been achieved. Accordingly, there is currently no full cure for osteoarthritis. However, osteoarthritis caused by cartilage damage, e.g., as a result of an injury, can sometimes be treated with autologous chondrocyte implantation. The adverse side effects of joint replacement surgery and autologous chondrocyte implantation include damage to blood vessels, dislocation, infection, instability, nerve damage, persistent pain, and weakness.

Gouty arthritis, or gout, is a congenital disorder involving uric acid metabolism. In gouty arthritis, monosodium urate or uric acid crystals are deposited on the articular cartilage of joints, tendons, and surrounding tissues due to elevated concentrations of uric acid in the blood stream. This provokes an inflammatory reaction of these tissues. The deposited crystals often increase in size and burst through the skin to form sinuses, discharging a chalky white material. Symptoms of gouty arthritis include acute inflammatory arthritis (a red, tender, hot, swollen joint), pain in the affected joint subsequent to warmth, swelling, and tenderness.

Temporary relief to the pain and reduction of the inflammation swelling that occurs in gout may be achieved with NSAIDs such as ibuprofen. The adverse side effects of ibuprofen are discussed above and below. Intraarticular glucocorticoids, administered via joint injection, are reserved for more serious cases of gout. Adverse side effects of glucocorticoids include immunosuppression, hyperglycemia, hypertension, and proteolysis. Long term use of glucocorticoids impairs many health anabolic processes. Colchicine was once the drug of choice for acute attacks of gout. However, colchicine impairs the motility of granulocytes. Also, colchicine sometimes has adverse side effects such as gastrointestinal upset, including diarrhea and nausea.

Other forms of arthritis include rheumatoid arthritis, psioriatic arthritis, and septic arthritis. Rheumatoid arthritis is a chronic systemic inflammatory disorder which affects many tissues and organs, but mainly attacks the joints producing an inflammatory synovitis that often results in destruction of the articular cartilage and ankylosis of the joints. Rheumatoid arthritis can also produce diffuse inflammation in the lungs, pericardium, pleura, and sclera as well as nodular lesions.

Psoriatic arthritis is an inflammatory condition typically affecting people suffering from the chronic skin condition psoriasis. There are five main types of psoriatic arthritis: symmetric psoriatic arthritis (affecting joints on both sides of the body), asymmetric psoriatic arthritis (typically involving less than three joints), spondylitis (stiffness of the spine, neck, hands or/and feet), arthritis mutilans (which can cause severe joint damage), and distal interphalangeal predominant psoriatic arthritis (inflammation and stiffness in the joints at the end of the fingers and toes). A large number of patients with psoriatic arthritis have fingernail deformities and, in severe cases, onycholysis (loss of nails). Psoriatic arthritis can also cause dactylitis and tendinitis.

Septic arthritis is caused by bacterial, mycobacterial, fungal, and viral joint infections. Bacteria commonly found to cause septic arthritis are *staphylococcus aureus* and *streptococcus*. Symptoms of septic arthritis include fever, intense joint pain, joint swelling, and *pseudoparalysis.*

As indicated above in connection with osteoarthritis and gouty arthritis, many techniques and medicines have been developed to treat the various types of arthritis. Unfortunately, treatment success is often slow and achieved only partially or not at all.

Bronchitis is an inflammation of the bronchi (medium-size airways) in the lungs. The symptoms of bronchitis include expectorating cough, shortness of breath (dyspnea), wheezing, occasionally chest pains, fever, and fatigue or malaise. Acute bronchitis is usually caused by viruses or bacteria and may last several days or weeks. Acute bronchitis, which is characterized by cough and phlegm (sputum) production and symptoms, is related to the obstruction of the airways by the inflammation and phlegm. Chronic bronchitis, which may arise from sources other than infection, is generally part of chronic obstructive pulmonary disease. Chronic bronchitis is characterized by persistent cough which produces phlegm.

Antibiotics are commonly used to treat bronchitis if a bacterial infection is suspected. The adverse side effects of antibiotics have been mentioned above. A bronchodilator, such as salbutamol, can be used to treat bronchitis but has adverse side effects including dry mouth, fine tremor, headache, muscle cramps, and palpitation.

Dry coughs caused by bronchitis are commonly treated with cough suppressants that suppress the body's urge to cough. Centrally acting cough suppressants, such as codeine and dextromethorphan, reduce the urge to cough by inhibiting the response of the sensory endings by depolarization of the vagus nerve. Adverse side effects associated with the use of codeine include itching, nausea, vomiting, drowsiness, urinary retention, and constipation. Dextromethorphan, when taken at higher than physician-recommended doses, is classified as a dissociative hallucinogenic drug. Because dextromethorphan can trigger a histamine release, use of dextromethorphan in atopic children is very limited. Productive coughs are treated with expectorants that loosen mucus from the respiratory tract. Guaifenesin, an expectorant drug commonly used for productive coughs, is generally effective but can cause adverse side effects including nausea, vomiting, and occasionally the formation of kidney stones of uric acid.

Hemorrhoids are varicosities or swelling and inflammation of rectal and anal veins. Both constipation and chronic diarrhea, which increase straining during bowel movements, can lead to hemorrhoids. Postponing bowel movements and fiber-deprived diet both lead to constipation and thus can cause hemorrhoids. Hemorrhoid symptoms include hematochezia (stool with blood), rectal and anal itching, pain, and swelling. For many people, hemorrhoids are mild and temporary conditions which heal spontaneously or by the same measures recommended for prevention.

No medicine is currently available for curing hemorrhoids. However, local treatments such as cold compresses, topical analgesics, and topical corticosteroids can provide temporary relief. Consistent use of topical analgesics during the early stages of a hemorrhoid flare-up can provide relief and stave off further development and irritation. However, topical analgesics such as dibucaine may cause allergic reactions including hives and swelling of the face, lips, tongue, and throat. Topical corticosteroids, such as hydrocortisone which contain steroid preparations, may weaken the skin and contribute to further flare-ups.

Urticaria, or hives, is a skin condition characterized by raised red skin welts. The welts can appear anywhere on the body, including the face, lips, tongue, throat, and ears. The welts typically itch severely, sting, and/or burn and often have a pale border. Urticaria is generally caused by direct contact with an allergenic substance or an immune response to food or some other allergen but can appear for other reasons.

Urticaria can be very difficult to treat. Most treatment plans involve being aware of what triggers urticaria. This can be problemsome because there are several different types of urticaria and people often exhibit more than one type. Also, symptoms are often idiopathic. Consequently, there might not be any clear trigger. If the triggers can be identified, then outbreaks can often be managed by limiting exposure to those triggers.

Drug treatment for urticaria is typically in the form of antihistamines. These are taken on a regular basis to produce a protective effect by lessening or halting attacks. For some people, antihistamines such as cimetidine and ranitidine may also help control symptoms either protectively or by lessening symptoms when an attack occurs. The use of cimetidine and ranitidine for urticaria is considered an off-label use because these two drugs are primarily used for the treatment of peptic ulcer disease and gastroesophageal reflux disease.

For very severe outbreaks, an oral corticosteroid such as prednisone is sometimes prescribed to treat urticaria. However this form of treatment is controversial due to the extensive adverse side effects common with corticosteroids and, as such, is not recommended as a long-term treatment option. None of these preceding urticaria treatments is a surefire means of controlling attacks. Some attacks seem to be treatment resistant. Medications can suddenly cease being as effective as they initially were.

A toothache is an aching pain in or around a tooth. Toothaches are generally caused by problems in the tooth or jaw, such as cavities, gum disease, the emergence of wisdom teeth, a cracked tooth, jaw disease, or/and or exposed tooth root. The causes of a toothache can also be a symptom of heart disease, such as angina or a myocardial infarction, due to referred pain. After having one or more teeth extracted, a condition known as dry socket can develop, leading to extreme pain.

Various analgesics, such as the over-the counter NSAID ibuprofen, can be effectively used to treat toothache pain. However, many of these analgesics have addictive and otherwise adverse side effects. For example, ibuprofen has been implicated in elevating cardiovascular risk such as myocardial infarction, particularly among persons chronically using high doses of ibuprofen. Other adverse side effects of ibuprofen use include nausea, gastrointestinal ulceration/bleeding, diarrhea, constipation, and hypertension.

Another drug commonly used for toothache pain is hydrocodone whose adverse side effects are varied and abundant. The main adverse side effects of hydrocodone use are respiratory effects which are very serious and commonly require the assistance of a physician. Hydrocodone can be habit forming, thereby leading to physical and psychological dependence on the drug. Other common adverse side effects of hydrocodone include nausea, sweating, constipation, vomiting, and euphoria.

Tinea pedis, commonly known as athlete's foot, is a parasitic fungal infection of the epidermis of the foot. Tinea pedis is typically caused by a mold, sometimes a yeast, which grows on the surface of the skin and then grows into the living skin tissue itself to produce the infection. The symptoms of tinea pedis include scaling, flaking, and itching of the affected skin. Blisters and cracked skin may also occur, leading to exposed raw tissue, pain, and swelling.

Tinea pedis is often treated with topical antifungal agents such as miconazole, ketaconazole, sertaconazole, or/and a keratolytic such as salicylic acid. These topical agents only clear the infection approximately 30% of the time and provide mycologic cures (absence of organisms) less than 15% of the time. The time for curing tinea pedis is typically long, often 45 days or more.

Acute viral nasopharyngitis, often known as the common cold, is an infectious viral disease of the upper respiratory system. Symptoms include sneezing, runny nose, nasal congestion, sore and phlegmy throat, coughing, headache, and tiredness. Acute viral nasopharyngitis is caused by rhinoviruses, corona viruses, human parainfluenza viruses, human respiratory syncytial viruses, adenoviruses, enteroviruses, metapneumovirus, and influenza viruses. In total, over 200 serologically different viral types cause acute viral nasopharyngitis.

There is currently no known cure for acute viral nasopharyngitis. Due to the many different types of viruses that cause acute viral nasopharyngitis and their tendency for continuous mutation, it is essentially impossible to gain complete immunity to acute viral nasopharyngitis. Treatment is limited to symptomatic supportive options, maximizing the comfort of the patient, and limiting complications and harmful sequelae.

Acute viral nasopharyngitis is self-limited. The host's immune system effectively deals with the infection. Within a few days after onset of acute viral nasopharyngitis, the body's humoral immune response begins producing specific antibodies for preventing the virus from infecting cells. Additionally, as part of the cell-mediated immune response, leukocytes destroy the particular virus through phagocytosis and infected cells to prevent further viral replication. In healthy immunocompetent people, the common cold goes away in seven days on average. An infected person often feels listless during the resolution period.

Dandruff is a medical condition that arises from excessive shedding of dead skin cells from the scalp. Some people, either chronically or as a result of certain triggers, experience an unusually large amount of skin flaking This may be accompanied by burning, redness, itching, and irritation of the scalp. The fungus malassezia furfur, found naturally on the skin surface of both healthy people and those with dandruff, has been cited as a cause of dandruff. However, it has recently been shown that a scalp specific fungus, malassezia globosa, may cause dandruff.

There are many treatments for dandruff. The most popular are topical zinc pyrithione, ketoconazole, and selenium sulfide. Although these treatments reduce the symptoms of dandruff, they do not eliminate it.

An itch is a sensation felt on an area of skin which causes a person to scratch the area. Itching can be related to anything from dry skin to cancer. The main chemical involved in itching is histamine, a molecule released by mast cells in the skin. Histamine causes itch and reddening as a result of insect bites.

A variety of anti-itch drugs, such as synthetic cortisol, are available to treat itching. Cortisol, a vital corticosteroid hormone produced by the adrenal cortex, is often referred to as the "stress hormone" because it is involved in the response to stress. The synthetic form of cortisol, termed hydrocortisone, can increase blood pressure and blood sugar levels and has an immunosuppressive action. Local anesthetics, such as benzocaine, can be used as anti-pruritics for treating itches but can cause allergic reactions including skin rash, hives, and swelling of the face, lips, or/and tongue.

Bromhidrosis, or body odor, is the smell of bacteria growing on the body. The bacteria multiply considerably in the presence of sweat. However, sweat itself is almost odorless. Bromhidrosis is associated with hair, feet, skin in general, armpits, genitals, and mouth. While bromhidrosis is sometimes believed to be the result of poor personal hygiene, bromhidrosis can be caused by changes in diet. Treatments for bromhidrosis include deodorants and perfumes which mask the smell but do not eliminate the odor.

Vaginitis, a common problem for women, is an inflammation of the vaginal mucosa and is often associated with an irritation or infection of the vulva leading to vulvovaginitis. Vaginitis may be asymptomatic, but usually leads to significant vaginal itching and irritation so that an infected woman self-medicates or seeks professional help. The woman may have inflammation, itching, burning, and swelling caused by the presence of extra immune cells and may notice a discharge. Vaginitis caused by infections includes bacterium (gardnerella), parasitic protozoan (trichomoniasis), and yeast (candidiasis). Vaginitis infections can progress through the uterus into the fallopian tubes and ovaries and lead to infertility.

Treatments for vaginitis include antibiotics and antifungal creams depending on the causative agent. Antibiotics such as metronidazole can effectively treat vaginitis caused by gardnerella and *trichomoniasis*. However, metronidazole has the above-mentioned adverse side effects. Antifungal creams including fluconazole can effectively treat vaginitis caused by candidiasis but may have adverse side effects such as abdominal pain, diarrhea, nausea, rash, and elevated liver enzymes. A cream containing cortisone can be used to relieve some of the irritation of vaginitis. If an allergic reaction arises with the use of cortisone, an antihistamine may be prescribed. Common adverse side effects of antihistamines are sedation, tinnitus, tremor, nausea, and vomiting.

Cancer is a class of diseases in which a group of cells display uncontrolled growth and intrusion, destruction of adjacent tissues, and metastasis. These three malignant properties of cancers differentiate from benign tumors, which are self-limited, and do not invade or metastasize. Most cancers form tumors.

Cancer often explodes in something akin to a chain reaction caused by a few errors, which compound into more severe errors. Errors which produce more errors are effectively the root cause of cancer, and also the reason that cancer is so difficult to treat. Even if the vast majority, typically millions, of cancerous cells can be effectively killed, the few remaining cancerous cells (and other error-prone precancerous cells) can self-replicate or send error-causing signals to other cells, thereby restarting the cancerous process.

Nearly all cancers are caused by abnormalities in the genetic material of the transformed cells. These abnormalities may be due to the effects of carcinogens such as tobacco smoke, radiation, certain chemicals, and infectious agents. Other cancer-promoting genetic abnormalities can be randomly acquired through errors in DNA replication, or are inherited, and thus present in all cells from birth.

Cancers caused by infection originate from viral pathogens. The main viruses associated with cancers are human papillomavirus, hepatitis B and hepatitis C virus, Epstein-Barr virus, and human T-lymphotropic virus. Liver cirrhosis, whether from chronic viral hepatitis infection or alcoholism, is associated with the development of liver cancer. The combination of cirrhosis and viral hepatitis presents the highest risk of liver cancer development. Worldwide, liver cancer is one of the most common, and most deadly, cancers due to a huge burden of viral hepatitis transmission and disease.

Common forms of cancer include carcinoma, sarcoma, leukemia, lymphoma, germ cell tumors, and blastic tumors. Carcinoma is a malignant tumor derived from epithelial including breast, prostate, lung, and colon cancer. Sarcoma includes malignant tumors derived from connective tissue or mesenchymal cells. Leukemia and lymphoma malignancies are derived from hematopoietic cells. Germ cell tumors are derived from totipotent cells. A blastic tumor or blastoma is usually a malignant tumor resembling an immature or embryonic tissue.

The symptoms of cancer can be divided into (1) local symptoms including unusual lumps or swelling (tumor), hemorrhage, pain and ulceration, and compression of surrounding tissues that can cause yellowing of the eyes and skin, (2) metastasis symptoms including enlarged lymph nodes, cough and hemoptysis, hepatomegaly, fracture of affected bones, and neurological symptoms, and (3) systemic symptoms, including weight loss, fatigue and cachexia, excessive sweating, anemia, and specific paraneoplastic phenomena.

Complete removal of the cancer without damage to the rest of the body is the goal of treatment. This can sometimes be accomplished by surgery, chemotherapy, radiation therapy, and/or cancer immunotherapy. The propensity of cancers to invade adjacent tissue or to spread to distant sites by microscopic metastasis often limits the effectiveness of surgery. The effectiveness of chemotherapy using anti-cancer drugs to destroy cancerous cells is often limited by toxicity to other tissues in the body, especially those tissues that have a high replacement rate, such as the intestinal lining. As to radiation therapy, the radiation dose to each cancerous site depends on a number of factors, including the radiosensitivity of each cancer type and whether there are tissues and organs nearby that can be damaged by radiation. Radiation therapy is thus not without adverse side effects to normal healthy tissues. In cancer immunotherapy, antibodies targeted to disease-causing antigens can be effective under certain circumstances. However, their efficacy may be limited by other factors. For instance, the microenvironment is immunosuppressive in the case of cancer tumors, thereby allowing even those tumors that present unusual antigens to survive and flourish in spite of the immune response generated by the cancer patient against his or her own tumor tissue.

Angiogenesis inhibitors prevent the extensive growth of blood vessels that tumors require to survive. Angiogenesis inhibitors, such as bevacizumab, have been approved and are in clinical use. One main problem with anti-angiogenesis drugs is that many factors stimulate blood vessel growth in normal or cancerous cells. Anti-angiogenesis drugs typically target the vascular endothelial growth factor pathway while other factors can continue blood vessel growth, e.g., vasculogenesis. Other problems include route of administration, maintenance of stability and activity, and targeting at the tumor vasculature.

Heart conditions and diseases constitute a spectrum of conditions that variously affect the heart, including the coronary blood vessels, in a debilitating manner. Major heart diseases and conditions include arrhythmias, cardiomyopathies, cardiovascular diseases, congenital heart defects, heart infections, and valvular heart diseases.

Arrhythmia, also known as cardiac dysrhythmia, is group of conditions in which the heart beat is abnormal due to abnormal electrical activity in the heart. The heart may beat too fast, too slow, or/and irregularly. Causes of arrhythmias include congenital heart defects, coronary artery disease, deformity of the heart, diabetes, excessive alcohol or caffeine use, hypertension, illicit substances, tobacco smoking, stress, and valvular heart disease. Symptoms of arrhythmias include chest pain, dizziness, fainting, shortness of breath, bradycardia, and tachycardia.

Medications to treat arrhythmias include antiarrhythmics, such as quinidine, and beta blockers, such as nebivolol. Quinidine can cause adverse side effects including granulomatous hepatitis, myasthenia gravis, thrombocytopenia, and torsades de pointes. Nebivolol can cause adverse side effects including bradycardia, depression, fatigue, and impotence.

Pacemakers or implantable cardioverter-defibrillators can be surgically implanted inside the body to emit electrical impulses for regulating the heartbeat. Complications of pacemaker surgery include abnormal heart rhythms, bleeding, and infection. Open-heart surgery to ameliorate arrhythmias may require many months for recovery. Also, adverse side effects of open-heart surgery include abnormal scar formations, atrial fibrillation, graft failure, myocardial infarction, serious bleeding, stroke, and artery, kidney, lung, and other organ problems. Although open-heart surgery can improve the quality of life, open-heart surgery can be complex, risky, and destructive due to its invasive nature, and is commonly considered a last treatment option.

Cardiomyopathy is a thickening, enlarging, and stiffening of the heart muscles. Symptoms of cardiomyopathy include bloating, breathlessness even at rest, fatigue, fainting, irregular heartbeats, and swelling of the legs, ankles, and feet. There are three forms of cardiomyopathy: dilated cardiomyopathy, hypertrophic cardiomyopathy, and restrictive cardiomyopathy. Dilated cardiomyopathy is generally the most common. In dilated cardiomyopathy, the heart's main pumping chamber, namely the left ventricle, becomes dilated. The pumping capability becomes inadequate for blood to flow to the heart. Hypertrophic cardiomyopathy involves abnormal growth or thickening of the heart and particularly affects the left ventricle. When thickening occurs in hypertrophic cardiomyopathy, the heart may stiffen. The area of the left ventricle may condense and thereby interfere with the heart's capability to deliver blood to the body. Restrictive cardiomyopathy occurs when the heart becomes stiff and less elastic. The heart ceases being able to properly expand and fill with blood between heartbeats. The specific causes of cardiomyopathies are not currently known.

Various treatments are available for cardiomyopathies. Medications include angiotensin II receptor antagonists, such as olmesartan, but have adverse side effects including diarrhea, dizziness, flu-like symptoms, headache, hyperglycemia, tachycardia, and upper respiratory tract infection. Angiotensin converting enzyme inhibitors such as enalapril can also be used. However, they have adverse side effects including cough, diarrhea, dizziness, electrolyte disorders, and vomiting, and can lead to very low blood pressure. Enalapril can inflict serious harm to a fetus if taken during pregnancy. Beta blockers such as nebivolol can be used but have adverse side effects including bradycardia, depression, fatigue, and impotence.

For dilated cardiomyopathy, pacemakers or implantable cardioverter-defibrillators can be implanted inside the body. Again, the complications of pacemaker surgery include abnormal heart rhythms, bleeding, and infection. A heart transplant can be performed for a severe cardiomyopathy. Adverse side effects of heart transplantation include bone loss, infections, ulcers, long recovery time, rejection of the donor heart, and possibly reduced life expectancy. A heart transplant is one of the most risky operations and should only be considered if other available treatments are unlikely to be successful.

Cardiovascular diseases arise when the blood vessels are narrow or blocked. The circulation of blood to the heart, brain, and other parts of the body becomes inadequate. Coronary heart diseases and ischaemic heart diseases are general forms of cardiovascular diseases. Atherosclerosis is a common cardiovascular disease that affects the arteries and can lead to coronary artery disease and peripheral artery disease. Symptoms of cardiovascular disease include angina, coldness, pain, shortness of breath, weakness, myocardial infarction, heart failure, stroke, and sudden cardiac death.

Medications for cardiovascular diseases include angiotensin converting enzyme inhibitors such as enalapril. Beta blockers such as nebivolol can also be used. The adverse side effects of enalapril and nebivolol have been mentioned above. Statins, including simvastatin, are commonly effective but have adverse side effects including headache, abdominal pain, constipation, diarrhea, weakness, chest pain, peripheral edema, and active liver diseases (hepatic encephalopathy). Simvastatin can cause harm to fetal development in nursing mothers.

Surgery for cardiovascular diseases includes coronary angioplasty and coronary artery bypass surgery. Coronary angioplasty involves placing a tube in a blocked artery, threading a balloon to the blocked artery, and inflating the balloon to reopen the artery. Serious risks of coronary angioplasty include aortic dissection, myocardial infarction, and stroke. Coronary artery bypass surgery involves removing the blocked portion of the artery and taking a vein from another part of the body to replace the diseased part of the artery. Adverse side effects of coronary artery bypass surgery include anesthetic complications, malignant hyperthermia, acute renal failure, chronic pain, chronic stress, hypoperfusion, keloid scarring, myocardial infarction, nonunion of the sternum, stenosis, and stroke.

Congenital heart defects typically develop while the baby is still inside the womb. The symptoms of congenital heart defects include cyanosis, shortness of breath during exercise, and swelling in the abdomen, feet, legs, and hands and around the eyes. The causes of congenital heart defects are not well understood. Genetics, medical conditions, and medications can be contributing factors of congenital heart defects.

Treatments for congenital heart defects include catheterization techniques, typically performed by inserting a catheter into a leg vein and guiding it to the heart with the assistance of radiology images. When the catheter is positioned at the site of the defect, tools are threaded through the catheter to the heart to repair the defect. Potential complications of a catheter include bleeding, blood clots, cardiac arrhythmias, cardiac tamponade, damage to the kidneys, hematoma, low blood pressure, and pain. One or more open-heart surgeries may be needed to fully correct the defect. The disadvantages of open-heart surgery have been mentioned above. An extreme option is a heart transplant, again a highly risky procedure.

Heart infections can be caused by inflammation, bacteria (streptococcus pyogenes which can lead to rheumatic fever, streptococcus pneumoniae, and brucella), viruses (adenovirus, coxsackie virus B, echovirus, Epstein-Barr virus, parvovirus B19, rubella virus, and sexually transmitted viruses), fungi (*candida albicans, aspergillus,* and *coccidioides*), and parasites (*trypanosoma cruzi* and *toxoplasma*). Some medications including antibiotics, such as penicillin and sulfonamide drugs, and illicit substances can cause heart infections. Other diseases that can cause heart infections include connective tissue disorders, lupus, vasculitis, and Wegener's granulomatosis.

Three common types of heart infections are endocarditis, myocarditis, and pericarditis. Endocarditis induces the inner membrane that apportions the chambers and valves of the heart (endocardium). Myocarditis induces the muscular median layer of the walls of the heart (myocardium). Pericarditis induces the tissue surrounding the heart (pericardium). Symptoms of heart infections include angina, coughing, fever, fatigue, rashes, shortness of breath, somnolence, swelling, syncope, heart palpitations, and myocardial infarction. Treatments for heart infections include antibiotics, angiotensin converting enzyme inhibitors, and beta blockers. All of these treatments can be effective. However, they have the above-mentioned adverse side effects and other disadvantages.

Valvular heart diseases involving the aortic, mitral, pulmonary, and tricuspid valves which open and close for directing blood flow through the heart can arise for many reasons including being born with the condition, connective tissue disorders, hereditary, high blood cholesterol levels, hypertension, increased age, inadequate hygiene, obesity, stress, tobacco smoking, infections, rheumatic fever, radiation treatments for cancer, and certain medications. Symptoms of valvular heart disease include chest pain, fatigue, fainting, heart murmur, irregular heartbeat, leaking, prolapse, shortness of breath, stenosis, and swollen feet or ankles Treatments for valvular heart disease vary depending on which valve is affected. Treatment options include medications and surgery. Medications include vasodilators such as adenosine, anticoagulants such as warfarin, and diuretics such as acetazolamide. Adverse side effects of adenosine include, allergic reactions, chest pain or pressure, dizziness, flushing of the face, headache, high blood pressure, tingling in the arms, and throat, neck, and jaw discomfort. Warfarin is contraindicated in pregnancy and can cause bleeding in the fetus, preterm birth, spontaneous abortion, stillbirth, and neonatal death. A common adverse side effect of warfarin is hemorrhage. A rare adverse side effect of warfarin is necrosis. Adverse side effects of acetazolamide include frequent urination, headaches, numbness and tingling in the fingers and toes, metabolic acidosis, parageusia, and increased risk of developing calcium oxalate and calcium phosphate kidney stone.

There are two main types for surgery involving the mitral valve, namely repair and replacement. Mitral valve repair typically consists of annuloplasty or valvuloplasty surgery that can preserve the valve Annuloplasty involves repairing the mitral valve by reconnecting valve leaflets or by abstracting surplus valve tissue, making the leaflets able to close tightly. Valvuloplasty consists of correcting the mitral valve to eliminate inverted blood flow.

Valvular valve replacement surgery involves replacing a damaged mitral valve with a prosthetic mechanical or tissue valve. Mechanical valves generally have a long shelf life. However, an anticoagulant medication such as warfarin may need to be used for the remainder of the person's life to prevent blood clots from forming on the valve. If a blood clot forms on the valve and disengages, the blood clot can travel to the brain and induce a stroke. Tissue valves are provided from an animal's tissue such as a pig's heart valve. While tissue valves generally do not last as long as mechanical valves, a long term anticoagulant medication may not be necessary with a tissue valve. Increased risks for anesthesia used in mitral valve surgery include arrhythmia, malignant hyperthermia, and seizures. Valve repair and replacement surgery requires open heart surgery and significant recovery time. Complications from valvular surgery include allergic reaction, bleeding, chronic pain, infection, keloid formation, myocardial infarction, and stroke.

Hypercholesterolemia, a lipid disorder, is a condition in which the blood has a high level of cholesterol. Closely related to hypercholesterolemia is hypertriglyceridemia, another lipid disorder in which excess triglycerides are present in the blood plasma. Hypercholesterolemia and hypertriglyceridemia arise when the blood contains excessive fatty substances. Abnormally high cholesterol and triglyceride levels can be caused by obesity, diet, metabolic syndromes, excessive alcohol consumption, family history, and certain medications, including birth control pills, beta blockers, certain antidepressants, and certain diuretics.

A lipid disorder increases risk of hypothyroidism, polycystic ovary syndrome, and kidney diseases. Lipid disorders also increase the risk of atherosclerosis and thus the risk of heart disease, myocardial infarction, stroke, and hypertension (high blood pressure). In leading to atherosclerosis, hypercholesterolemia can specifically lead to arrhythmias, arterioles, bacterial endocarditis, cardiomyopathy, cerebrovascular accident, cerebrovascular disease, coronary artery disease, Kawasaki disease, diseases of pulmonary circulation, diseases of veins and lymphatics, and other diseases of the circulatory system.

Atherosclerosis arises when an artery wall thickens due to the build-up of cholesterol, fat, or/and other substances on the artery wall. The build-up can harden and form plaque, making the artery narrow. Eventually it becomes difficult for blood to flow through the artery. The blood can clot, i.e., undergo thrombus. When thrombus occurs in the heart, angina, shortness of breath, and myocardial infarction can occur. If thrombus occurs in the brain, a stroke can occur. Thrombus in the limbs can result in claudication (impairment in walking) Because atherosclerosis can be systemic, other undesirable medical conditions can occur in the intestines, kidneys, and lungs. In addition to the causative factors mentioned above for abnormally high cholesterol and triglyceride levels, atherosclerosis can arise from diabetes, high blood pressure, increasing age, and tobacco smoking The first line of treatment for atherosclerosisis is preferably exercising and a well balanced diet with plenty of fiber-rich fruits and vegetables and avoidance of saturated fats and trans-fatty acids. Medications to treat atherosclerosis include statins, such as simvastatin and clopidogrel, to treat plaque and lower cholesterol. Simvastatin has the adverse side effects mentioned above. Clopidogrel, a oral antiplatelet agent, can inhibit thrombus but has the adverse side effects of hemorrhage, neutropenia, abdominal pain, chest pain, and headache.

Diabetes mellitus is a chronic disease in which there is a high level of glucose, or sugar, in the blood. Insulin is a hormone produced by the pancreas to manage glucose and is required to move glucose from the bloodstream into liver cells, muscles, and fat so that the glucose can be used as fuel to provide energy for the body. Diabetes mellitus generally arises when the pancreas does not manufacture enough insulin or/and liver cells, muscles, and fat do not respond properly to insulin.

Diabetes mellitus can harm blood vessels and nerves. As a result, individuals with diabetes mellitus commonly have foot problems. In severe, circumstances an affected foot may need to be amputated. Diabetes is one of the most common causes of amputations.

The three major forms of diabetes mellitus are diabetes type 1, diabetes type 2, and gestational diabetes. Diabetes type 1 is usually identified during childhood but can be identified in persons over 20 years old. While the precise cause of diabetes type 1 is relatively unknown, diabetes type 1 can arise due to genetics, autoimmune conditions, or/and viruses. Diabetes type 2 is more common than diabetes type 1 and typically occurs in adults. Gestational diabetes is high blood glucose that can develop in a woman during pregnancy. Other forms of diabetes mellitus include congenital diabetes, cystic fibrosis-related diabetes, steroid diabetes, and forms of monogenic diabetes.

Diabetes mellitus is debilitating and can cause numerous adverse medical conditions including atherosclerosis, blindness, cardiovascular diseases, chronic renal failure, congenital cardiac disease, chronic pancreatitis, coronary artery disease, Cushing's syndrome, diabetic dermadromes, elevated cholesterol levels, erection problems, fatty liver, Friedreich's ataxia, haemochromatosis type 1, heart diseases, hyperlipidemia, hypoglycemia, kidney failure, metabolic disorders, myotonic dystrophy, peripheral vascular diseases, retinal damage, ulcers, several mitochondrial neuropathies, and myopathies. Individuals with diabetes mellitus can suddenly undergo a severe attack such as diabetic ketoacidosis in which there is an absolute shortage of insulin. Another severe condition is nonketotic hyperosmolar coma in which the body is dehydrated due to loss of body water. Acute or prolonged hypoglycemia, arising, for example, from diabetes mellitus, can lead to brain damage, paralysis, or death.

There is currently no effective cure for diabetes mellitus. Prevention involves maintaining a healthy low-fat diet and exercise to balance the sugar level in blood, blood pressure, and cholesterol. Medications to treat diabetes include insulin to assist in lowering the glucose level.

There are various difficulties with insulin for treatment of diabetes mellitus including the mode of administration, selecting the correct dosage, timing of the dosage, and variability in absorption. If too much or too little insulin is delivered, hyperglycemia can be induced. Adverse side effects of insulin reaction include convulsions, confusion, headache, unconsciousness, and weakness. If the use of insulin results in the body cells not absorbing blood glucose, a hypoglycemic coma can occur.

Ocular conditions consist of irritations and infections of the visual pathways including the eyes and eyelids. Some eye problems are minor and transient. Others can lead to loss of vision. Common eye problems include conjunctivitis, trachoma, and uveitis.

Conjunctivitis (pink eye) is inflammation or infection of the membrane lining the conjunctiva (eyelids). Symptoms of conjunctivitis include blurred vision, chemosis (irritation), epiphora (watering), hyperaemia (redness), and pain. Individuals with conjunctivitis frequently have difficulty opening their eyes after sleeping for extended periods due to dried crusts or mucus on the eyelids. Conjunctivitis can be caused by allergenic (hay fever), bacterial (chlamydia trachomatis or moraxella), chemical and related irritant (fumes, pet hairs, and use of contact lenses), and viral (adenovirus) conditions.

There are a number of types of conjunctivitis, each with its own treatment. Allergenic conjunctivitis is treated with antihistamines and NSAIDs which have the above-mentioned adverse side effects. Bacterial conjunctivitis can be treated with antibiotic eye drops. The adverse side effects of such treatment range from fever and nausea to major allergic reactions. There is currently no specific treatment for viral conjunctivitis. Cold compress and artificial tears may provide symptomatic relief for viral conjunctivitis. Moderate conjunctivitis due to chemicals and irritants can be treated effectively with saline solution. However, major chemical burns of the eyes can lead to severe eye problems.

Trachoma is an infectious eye disease, generally caused by the bacteria chlamydia trachomatis and is spread by individuals, inanimate objects, and flies. Trachoma symptoms include cloudy cornea, corneal scarring, eye discharge, swollen eyelids, swelling of lymph nodes in front of the ears, and trichiasis in which the eyelashes are turned in. Trichiasis can result in eye ulcers, additional scarring, vision loss, and possibly blindness.

Techniques to avoid trachoma include keeping the face and environment clean. Trachoma can be effectively treated with antibiotics, such as erythromycin and doxycycline, if applied sufficiently early, e.g., before the development of scarring and lid deformities. The adverse side effects of antibiotics have been mentioned above. Antibiotics should not be used in pregnant and nursing women due to potential damage to the fetus and child.

Uveitis is an inflammation of the interior of the eye. Uveitis can be categorized anatomically into anterior, intermediate, posterior, and panuveitic forms based on which part of the eye is affected by the inflammation. The symptoms of uveitis include dark floating spots in vision, eye pain, redness of the eyes, and sensitivity to light (photophobia). Serious complications include band keratopathy, cataracts, glaucoma, retinal edema, retinal detachment, and vision loss.

Uveitis is typically treated with corticosteroids administered orally or as eye drops. High doses of corticosteroids, e.g., 100 mg per day, must be used to treat severe and acute posterior uveitis. Such doses can cause severe complications. Thus, the administered amounts need to be reduced when clinical improvement occurs. However, reduction below 15-20 mg per day can lead to reoccurrences of the disease. In addition, corticosteroids have a number of adverse side effects as mentioned above.

The human ear consists of three parts referred to as the outer, middle, and inner ears. The outer ear, including the ear canal, collects sound waves. The middle ear, which is separated from the outer ear by the eardrum, amplifies the sound waves. The inner ear converts the amplified sound waves into electrical impulses that are sent to the brain. An array of conditions affect the hearing or/and balance of the body. Ear problems include Ménière's disease, tinnitus, and infections including otitis media, a common illness in infants and children.

Ménière's disease is an inner ear disorder that disturbs hearing and balance. The specific cause of Ménière's disease is not currently known. Ménière's disease affects the labyrinth in the inner ear. The labyrinth is a system of tiny channels filled with endolymph (fluid). Ménière's disease causes the endolymph to build up, disrupting both hearing and balance. Increase of the endolymph can cause the membranous labyrinth to dilate and lead to endolymphatic hydrops. Symptoms of Ménière's disease include vertigo, hearing loss, tinnitus, sensation of fullness, or/and pressure in ears. Ménière's disease can cause migraines to escalate.

There is currently no cure for Ménière's disease. Treatments for Ménière's disease include lipoflavonoid, the meniett device, and surgery. Lipoflavonid can sometimes help but is not approved by the U.S. Food and Drug Administration and can cause hives, upset stomach, and headaches. The meniett device provides transtympanic micropressure pulses that can reduce the frequency of vertigo but are not suitable for individuals with acoustic neuroma or brain tumor, erilymph fistula, etrocochlear damage, and low-pressure hydrocephalus. Surgery for treating Ménière's disease can consist of chemical labyrinthectomy in which an antibiotic (gentamicin) is injected into the inner ear for eradicating the vestibular apparatus. Alternatively, vestibular neurectomy surgery can be performed by sectioning the nerve of balance where it comes out of the brain while preserving the hearing portion of the nerve of balance. These types of surgery can eliminate vertigo but are destructive and are generally limited to individuals affected in one ear with Ménière's disease.

Tinnitus is the perception of sound within the ear in the absence of corresponding external sound. The causes of tinnitus are numerous and include excessive loud noises, aging, ear infections, genetics, and hundreds of medications such as analgesics, NSAIDs, and antibiotics. In many other cases, the specific cause of tinnitus cannot be established. Tinnitus is usually described as ringing or/and screaming sounds. Persons having tinnitus may have trouble hearing along with loss of concentration and loss of sleep.

If tinnitus is moderate, physical movements of the head, jaw, shoulder, tongue, and eyes can reduce the symptoms. Tinnitus can be treated with benzodiazepines such as clonazapam and lorazepam. Benzodiazepines have many adverse side effects including drowsiness, addiction, depression, euphoria, libido, and erection problems. Benzodiazepines taken during pregnancy can have adverse effects on the baby. Sudden withdrawal of benzodiazepines in pregnant women can result in spontaneous abortions.

Otitis media is an inflammatory infection of the middle ear. Otitis media infection can be caused by bacterial (haemophilus influenzae, Moraxella catarrhalis, and streptococcus pneumoniae), fungal (*aspergillus* and *candida*), and viral (respiratory syncytial virus) pathogens. When otitis media occurs, pressure builds up behind the tympanic membrane (eardrum) causing pain, and the middle ear becomes clogged with fluid and mucus. Symptoms of otitis media include Eustachian tube dysfunction, exudative inflammation, fever, meningism, severe pain, muffled noise in ear, deafness, and sensitive mastoid process.

Otitis media can be treated with analgesics such as ibuprofen, topical agents such as antipyrine and benzocaine ear drops, antibiotics such as amoxicillin, and surgery. Ibuprofen has the adverse side effects mentioned above. Antipyrine and benzocaine ear drops can cause adverse side effects such as itching, rash, and swelling of the mouth, face, lips, or/and tongue. Amoxicillin has various adverse side effects including allergic reactions and diarrhea. In chronic cases or with effusions, surgery can be performed by inserting a tympanostomy tube into the eardrum. This allows air to pass through and discharges pressure and excess fluids. The adverse affects of such surgery include a permanent hole in the eardrum, damage to the outer ear, ongoing fluid discharge from ear, scarring of the eardrum, and possible hearing loss.

The urethra is a tube which bridges the urinary bladder and allows the release of urine and other substances. The external urethral sphincter is a muscle that conducts the voluntary control of urination. Urethral disorders include urethral stricture and urethritis.

Urethral stricture is an abnormal narrowing of the opening of the urethra. Urethral strictures can be caused by injury related trauma, bacteria or viral infections especially sexually transmitted diseases, scar tissue from surgery, and the transmission of painful kidney stones. In babies, urethral strictures can result from circumcision. Symptoms of urethral strictures include decreased urinary stream, discharge from the urethra, enlarged or tender lymph nodes, and swelling. Urethral stricture can cause benign prostatic hyperplasia, Skene's gland, bilateral hydronephrosis, hernia, and urethral diverticulum.

There are currently no drug treatments for curing urethral strictures. Surgical treatments for urethral strictures include cytoscopy, urethrotomy, and urethroplasty. Cytoscopy consists of inserting an instrument into the urethra to widen it. In urethrotomy, small cuts are made in the urethra to widen it. Urethroplasty involves removal of the diseased portion and connection of the strictures if they are short or, for long strictures, implanting with tissue from the perineum or scrotum. After surgery, patients may have a stinging pain, small amounts of blood, and incontinence in urination. Patients may also have impaired sexual function, abdominal pains, and muscle spasms. Though these forms of surgery can be effective, surgery can be painful and risky.

Urethritis is an inflammatory infection of the urethra. Urethritis infections can arise from viruses such as adenovirus, herpes simplex viruses, *Escherichia coli*, chlamydia, gonorrhea, and mycoplasma genitalium. Other causative agents of urethritis include chemicals (contraceptive jellies and spermicides) and injuries. Symptoms of urethritis includes dysuria (painful or difficult urination), abdominal pain, blood in the urine, discharge, fever, recurrent or/and urgent urination, itching, tenderness, swelling in the groin area, and pain with intercourse.

Various drugs can be used to treat urethritis including co-trimoxazole and metronidazole. Co-trimoxazole has adverse side effects including upset stomach, fever, mouth sores, skin rash, and yellowing of the skin or/and eyes. Once again, metronidazole has the above-mentioned adverse side effects.

Sporkenbach et al. ("Sporkenbach"), U.S. Pat. No. 4,404, 191, discloses a viricide technique for inactivating viruses on animate and inanimate surfaces by contacting the surfaces with a salt of peroxymonosulfuric acid ($H_2SO_5$) commonly known as Caro's acid. The peroxymonosulfuric acid salt, applied from an aqueous solution, can be a salt of an alkali metal such as potassium, sodium, or lithium, a salt of an alkaline earth metal such as calcium or magnesium, or an ammonium salt. Sporkenbach preferably employs $KHSO_5$ as the peroxymonosulfuric acid salt. $KHSO_5$ is provided from the mixed triple salt having the chemical formula $2KHSO_5.KHSO_4.K_2SO_4$ where $KHSO_4$ is potassium hydrogen sulfate and $K_2SO_4$ is potassium sulfate sometimes referred to as dipotassium sulfate.

$KHSO_5$ and $2KHSO_5.KHSO_4.K_2SO_4$ each have multiple chemical names. Both $KHSO_5$ and $2KHSO_5.KHSO_4.K_2SO_4$ are commonly referred to as "potassium monopersulfate". To avoid confusion, $KHSO_5$ is referred to herein as "potassium hydrogen peroxymonosulfate" or simply "potassium peroxymonosulfate". $2KHSO_5.KHSO_4.K_2SO_4$ is referred to herein as "potassium monopersulfate triple salt" or sometimes simply as "potassium monopersulfate".

Sporkenbach identifies poliovirus, coxsackie virus, simian vacuolating virus 40 and adenovirus as being inactivated by potassium hydrogen peroxymonosulfate. Poliovirus causes poliomyelitis. There are two forms of coxsackie virus, type A and type B. Coxsackie A virus causes hand, foot, and mouth disease, acute haemorrhagic conjunctivitis, herpangina, and aseptic meningitis which includes viral meningitis. Coxsackie B virus causes pleurodynia (Bornholm disease) and can induce aseptic meningitis and diabetes mellitus type 1. Simian vacuolating virus 40 can cause tumors and cancer. Adenovirus generally produces infections in the upper respiratory tract. Adenovirus infections often appear as gastroenteritis, conjunctivitis, cystitis, and rash illness. Symptoms of respiratory illness caused by adenovirus infection include acute viral nasopharyngitis, pneumonia, croup, and bronchitis.

Sporkenbach discloses that its viricide technique can disinfect inanimate surfaces such as walls, floors and work surfaces, hospital utensils, and surgical and dental instruments in industrial, domestic, and medical environments and animate surfaces such as the skin of human and non-human animals during presurgical preparation in human and veterinary medicine. While Sporkenbach's viricide technique may prevent the diseases caused by the preceding viruses from being contracted, Sporkenbach's technique does not help already-infected people recover from those diseases.

Auchincloss, U.S. Pat. No. 4,822,512, discloses a dry water-soluble biocide for inactivating certain types of viruses, bacteria, and mold on non-human animals, specifically chickens, pigs, cows, and horses. The biocide contains (a) 0.01 to 5 parts by weight of a water-soluble inorganic halide, (b) 25 to 60 parts by weight of an oxidizing agent which reacts, in aqueous solution, with the halide to generate hypohalite ions, (c) 3 to 8 parts by weight of sulfamic acid, and (d) 10 to 30 parts by weight of an anhydrous alkali metal phosphate subject to the total parts totaling 100. The biocide may include up to 20 parts by weight of a non-reducing organic acid and up to 20 parts by weight of an organic surfactant.

The preferred oxidizing agent in Auchincloss's biocide is a persulfate or a peroxyphthalate. A persulfate is a sulfur-oxygen-containing compound having more oxygen than a normal sulfate. The additional oxygen in a persulfate is present in the form of one or more peroxide units, a peroxide being a chemical compound which includes an oxygen-oxygen single bond. The main types of persulfates are peroxymonosulfates and peroxydisulfates. A peroxyphthalate is a compound having more oxygen than a normal phthalate, the additional oxygen likewise being present in the form of one or more peroxide units.

Auchincloss's oxidizing agent is normally potassium monopersulfate triple salt, i.e., $2KHSO_5 \cdot KHSO_4 \cdot K_2SO_4$. The halide is preferably sodium chloride but can be potassium chloride, potassium bromide, potassium iodide, sodium bromide, or sodium iodide. The organic acid is preferably malic or succinic acid. The alkali metal phosphate can be any one of sodium hexametaphosphate, monosodium phosphate, disodium phosphate, trisodium phosphate, tetrasodium pyrophosphate, monopotassium phosphate, dipotassium phosphate, tripotassium phosphate, and tetrapotassium pyrophosphate. According to Auchincloss, one embodiment of the biocide apparently consisted of 1.5 parts of sodium chloride, 50 parts of potassium monopersulfate triple salt, 10 parts of sulfamic acid, 5 parts of malic or succinic acid, 18.5 parts of sodium hexametaphosphate and (possibly) other alkali metal phosphate, and 15 parts of sodium dodecylbenzene sulfonate as the surfactant.

Auchincloss reported generally good results in variously using its biocide to disinfect chickens, pigs, cows, and horses. Auchincloss also reported that chickens can drink the biocide (apparently without harm), the biocide is not a skin or eye irritant, it is possible to bathe in the biocide (likewise apparently without harm), and the biocide can be sprayed in occupied rooms without causing discomfort.

Potassium peroxymonosulfate triple salt used by Sporkenbach and Auchincloss is commercially available from various sources including E.I. Dupont de Nemours and Company under the trade name Oxone and United Initiators under the trade name Caroat. Potassium hydrogen peroxymonosulfate, the principal component of potassium peroxymonosulfate triple salt, is a strong oxidizing agent. For instance, potassium hydrogen peroxymonosulfate can convert halide ions into halogens, ferrous ions into ferric ions, manganous ions into manganic ions, and hydrogen peroxide into oxygen. Potassium hydrogen peroxymonosulfate can also initiate the free radical polymerization of vinyl monomers such as vinyl acetate, ethyl acrylate, and acrylonitrile. In addition to the uses mentioned above, potassium hydrogen peroxymonosulfate serves as a bleaching agent in denture cleansers, toilet-bowl cleaners, and laundry/dry bleaches.

Valliéres, U.S. Pat. No. 5,186,946, discloses a disinfectant reportedly effective against bacteria, fungi, bacterial and fungal spores, and viruses. Somewhat similar to Auchincloss's composition, Valliéres' disinfectant consists of 60 to 90 weight % potassium hydrogen peroxymonosulfate, 2-10 weight % malic acid, 2-6 weight % sulfamic acid, 0.25-3 weight % ethylene diamine tetraacetic acid disodium salt, and 1-15 weight % alkylated ether of polyethylene glycol surfactant. Different from Auchincloss, Valliéres avoids the chlorine present in the sodium chloride preferably used by Auchincloss to implement the inorganic halide in Auchincloss's biocide. Valliéres states that its disinfectant is to be used for cleaning instruments, floors, and bedding in hospitals, bio-medical research centers, health centers, veterinary hospitals, and clinics.

Potassium hydrogen peroxymonosulfate is also used for removing chloramines in swimming pools. Regarding swimming pools, Lightcap et al. ("Lightcap"), U.S. Pat. No. 7,560,033 B2, discloses an anhydrous composition formed with potassium hydrogen peroxymonosulfate and an active halogen agent for sanitizing water in recirculating water systems such as swimming pools. The active halogen agent consists of an alkali metal salt of dichloro-s-triazinetrione or/and halogenated dimethylhydantoin. Lightcap reports that its composition inhibited the growth of algae in water and inactivated *E. coli* and *Enterococcus faecium* bacteria in water.

Randeri et al. ("Randeri"), U.S. Pat. No. 3,873,696, discloses that contact lenses can be effectively cleaned with a solution containing an oxygen-releasing salt such as a thiosulfate, a persulfate, or a peroxydisulfate. Randeri's preferred oxygen-releasing salt is potassium hydrogen peroxymonosulfate provided from a triple salt also containing potassium hydrogen sulfate ($KHSO_4$) and potassium sulfate ($K_2SO_4$). Randeri's solution normally contains a chloride-ion-releasing salt such as sodium chloride.

Potassium monopersulfate triple salt of the chemical formula $2KHSO_5 \cdot KHSO_4 \cdot K_2SO_4$ is an implementation of the more general chemical composition $(KHSO_5)_x (KHSO_4)_y (K_2SO_4)_z$ where x, y, and z are variable mole (or molar) fractions whose sum is 1. The general composition $(KHSO_5)_x (KHSO_4)_y (K_2SO_4)_z$ is referred to herein as "potassium monopersulfate triple salt composition" where the word "composition" distinguishes $(KHSO_5)_x (KHSO_4)_y (K_2SO_4)_z$ from the specific formulation $2KHSO_5 \cdot KHSO_4 \cdot K_2SO_4$. When mole fractions x, y, and z respectively are 0.5, 0.25, and 0.25, the potassium monopersulfate triple salt composition $(KHSO_5)_x (KHSO_4)_y (K_2SO_4)_z$ becomes potassium monopersulfate triple salt of the formula $2KHSO_5 \cdot KHSO_4 \cdot K_2SO_4$.

The weight (mass) fractions of potassium hydrogen peroxymonosulfate ($KHSO_5$), potassium hydrogen sulfate ($KHSO_4$), and potassium sulfate ($K_2SO_4$) respectively are roughly 45%, 25%, and 30% in a common formulation of potassium monopersulfate triple salt composition $(KHSO_5)_x(KHSO_4)_y(K_2SO_4)_z$. The active oxygen content for this formulation is approximately 4.7%. A small percentage of potassium persulfate (or potassium perdisulfate) of the chemical formula $K_2S_2O_8$ may be present in potassium peroxymonosulfate triple salt composition and in the specific potassium peroxymonosulfate triple salt. The potassium persulfate is generally undesirable because it reduces the active oxygen content, e.g., to 4.5%. A higher active oxygen content is often desired.

Potassium peroxymonosulfate triple salt composition $(KHSO_5)_x(KHSO_4)_y(K_2SO_4)_z$, including potassium peroxymonosulfate triple salt $2KHSO_5.KHSO_4.K_2SO_4$ itself, can be manufactured in various ways. Martin, U.S. Pat. No. 7,090,820 B2, discloses a technique for manufacturing the potassium monopersulfate triple salt composition $(KHSO_5)_x(KHSO_4)_y(K_2SO_4)_z$ with mole fractions x, y, and z adjusted to achieve an active oxygen content greater than 4.5% and with a reduced content of potassium persulfate. In a first embodiment, x is 0.43-0.64, y is 0.15-0.43, and z is 0.15-0.43. In a second embodiment, x is 0.46-0.64, y is 0.15-0.37, and z is 0.15-0.37.

Martin's process for manufacturing the potassium triple salt composition so that mole fractions x, y, and z fall into the ranges of the second embodiment entails adding a hydrogen peroxide solution containing at least 70% hydrogen peroxide by weight to a sulfuric acid solution containing at least 90% sulfuric acid by weight at a sulfuric-acid-to-hydrogen-peroxide ratio which is substoichiometric to produce a first Caro's acid solution containing peroxymonosulfuric acid (again, $H_2SO_5$) and hydrogen peroxide. The first Caro's acid solution is combined with oleum containing sulfuric acid and sulfur trioxide. The oleum reacts with water in the first Caro's acid solution to produce a second Caro's acid solution. An alkali potassium compound is added to the second Caro's acid solution to produce a partially neutralized solution containing potassium monopersulfate triple salt composition $(KHSO_5)_x(KHSO_4)_y(K_2SO_4)_z$ in which x, y, and z have values in the ranges of Martin's second embodiment.

Looking now at the background art in total, bacterial, eukaryotic, prion, and viral pathogens cause many diseases to human. Success in treating these diseases varies widely. While treatments for some of these diseases are essentially fully successful, treatments for others are only partially successful or do not currently exist. In particular, treatments for allergic rhinitis, arthritis, bronchitis, hemorrhoids, urticaria, toothache, tinea pedis, acute viral nasopharyngitis, herpes simplex, dandruff, itching, bromhidrosis, and vaginitis are commonly weak or non-existent. Even when treatments are fully or partially successful, there are often adverse side effects to the treatments.

Sporkenbach's technique of using a peroxymonosulfuric acid salt, preferably potassium hydrogen peroxymonosulfate, to inactivate certain viruses on animate and inanimate surfaces is an advancement. However, Sporkenbach's viricide technique is not useful in treating people to recover from the diseases caused by those viruses. It is desirable to have better technique for treating people infected with diseases caused by bacterial, eukaryotic, prion, and viral pathogens. It is especially desirable to have better techniques for treating allergic rhinitis, arthritis, bronchitis, hemorrhoids, urticaria, toothache, tinea pedis, acute viral nasopharyngitis, herpes simplex, dandruff, itching, bromhidrosis, and vaginitis without causing significant adverse side effects.

General Disclosure of the Invention

The present invention provides such enhanced techniques for treating people infected with diseases and other debilitating medical conditions caused by bacterial, eukaryotic, prion, and viral pathogens and by non-pathogenic inflammation. The techniques of the invention can also be used for preventing people from being infected with debilitating medical conditions caused by bacterial, eukaryotic, prion, and viral pathogens and by non-pathogenic inflammation. The present treatment/prevention techniques have been successfully demonstrated for treating allergic rhinitis (hay fever), arthritis, bronchitis, hemorrhoids, urticaria (hives), toothache, tinea pedis (athlete's foot), acute viral nasopharyngitis (common cold), herpes simplex (herpes simplex 1 or/and herpes simplex 2), dandruff, itching, bromhidrosis (body odor), and vaginitis without causing significant adverse side effects.

More particularly, in a first aspect of the invention, a medicinal drug formed at least partially with salt, i.e., one or more individual salts, of peroxymonosulfuric acid is administered sufficiently to a person to treat a medical condition contracted by the person or/and to prevent the person from contracting the medical condition. The medical condition includes one or more of a bacterial infection, a eukaryotic infection, a prion-caused infection, and a non-pathogenic-caused inflammation. To the extent not covered by these four types of medical conditions, the medical condition includes a fungal infection, a spore-caused infection, and a parasitic infection. The medical condition specifically includes each of allergic rhinitis, arthritis, hemorrhoids, urticaria, toothache, tinea pedis, herpes simplex, dandruff, itching, bromhidrosis, and vaginitis. The medicinal drug can be administered in various ways, including topically, orally, intranasally, intraotically, vaginally, rectally, urethally, or/and by injection.

In a second aspect of the invention, a medicinal drug formed at least partially with salt of peroxymonosulfuric acid is administered non-topically, e.g., orally, intranasally, intraotically, vaginally, rectally, urethally, or/and by injection, sufficiently to a person to treat a virus-caused medical condition contracted by the person or/and to prevent the person from contracting the virus-caused medical condition. The virus-caused medical condition can be bronchitis or/and acute viral nasopharyngitis.

The salt of peroxymonosulfuric acid in the treatment techniques in the first two aspects of the invention is normally at least one of alkali metal salt, alkaline-earth metal salt, and ammonium salt. The peroxymonosulfuric acid salt preferably includes potassium hydrogen peroxymonosulfate typically at least partially provided as a component of a multiple salt composition.

In a third aspect of the invention, a medicinal drug formed at least partially with potassium monopersulfate triple salt composition is administered sufficiently to a person to treat a medical condition contracted by the person or/and to prevent the person from contracting the medical condition. As in the first aspect of the invention, the medical condition in the third aspect of the invention includes one or more of a bacterial infection, a eukaryotic infection, a prion-caused infection, and a non-pathogenic-caused inflammation. To the extent not covered by these four types of medical conditions, the medical condition in the third aspect of the invention also includes a fungal infection, a spore-caused infection, and a parasitic infection. The medical condition in the third aspect of the invention likewise specifically includes each of allergic rhinitis, arthritis, hemorrhoids, urticaria, toothache, tinea pedis, herpes simplex, dandruff, itching, bromhidrosis, and vaginitis. The medicinal drug in the treatment technique of the third aspect of the invention can be administered in various ways, likewise including topically, orally, intranasally, intraotically, vaginally, rectally, urethally, or/and by injection.

In a fourth aspect of the invention, a medicinal drug formed at least partially with potassium monopersulfate triple salt composition is administered non-topically, e.g., orally, intranasally, intraotically, vaginally, rectally, urethally, or/and by injection, sufficiently to a person to treat a virus-caused medical condition contracted by the person or/and to prevent the person from contracting the medical condition. As in the second aspect of the invention, the virus-caused medical condition in the fourth aspect of the invention can be bronchitis or/and acute viral nasopharyngitis.

In a fifth aspect of the invention, a medicinal drug formed at least partially with inorganic halide and an oxidizing agent reactable in water with the halide to generate hypohalite ions is administered sufficiently to a person to treat a medical condition contracted by the person or/and to prevent the person from contracting the medical condition. The oxidizing agent preferably includes salt of peroxymonosulfuric acid. Other materials used in forming the medicinal drug in the fifth aspect of the invention normally include alkali metal phosphate and sulfamic acid.

The ratio of the mole fraction of the inorganic halide to the mole fraction of the active oxygen-releasing material is normally 0.01-4. The ratio of the mole fraction of the metal phosphate to the mole fraction of the active oxygen-releasing material is normally 0.4-40. The ratio of the mole fraction of sulfamic acid to the mole fraction of the active oxygen-releasing material is normally 0.03-30.

The medicinal drug in the fifth aspect of the invention is also normally formed at least partially with a non-reducing organic acid and/or a surfactant. The ratio of the mole fraction of the non-reducing organic acid to the mole fraction of the active oxygen-releasing material is normally 0.01-50. The ratio of the mole fraction of the surfactant to the mole fraction of the active oxygen-releasing material is normally 0.03-30.

As in the first two aspects of the invention, the salt of peroxymonosulfuric acid in the treatment techniques in the fifth aspect of the invention is normally at least one of an alkali metal salt, an alkaline-earth metal salt, and an ammonium salt. The peroxymonosulfuric acid salt in the fifth aspect of the invention likewise preferably includes potassium hydrogen peroxymonosulfate typically at least partially provided as a component of a multiple salt composition. The potassium hydrogen peroxymonosulfate then forms the active oxygen-releasing material of the oxidizing agent.

The medical condition in the fifth aspect of the invention includes one or more of a bacterial infection, a eukaryotic infection, a prion-caused infection, a viral infection, and a non-pathogenic-caused inflammation. To the extent not covered by these five types of medical condition, the medical condition in the fifth aspect of the invention also includes one or more of a fungal infection, a spore-caused infection, and a parasitic infection. The medical condition in the fifth aspect of the invention specifically includes each of allergic rhinitis, arthritis, bronchitis, hemorrhoids, urticaria, toothache, tinea pedis, acute viral nasopharyngitis, herpes simplex, dandruff, itching, bromhidrosis, and vaginitis. As in the treatment techniques of the first and third aspects of the invention, the medicinal drug in the treatment technique of the fifth aspect of the invention can be administered in various ways, including topically, orally, intranasally, intraotically, vaginally, rectally, urethally, or/and by injection.

In brief, a medicinal drug formed at least partially with peroxymonosulfate, preferably potassium hydrogen peroxymonosulfate, or a group of components including peroxymonosulfate or/and a similarly acting oxidizing agent is utilized in accordance with the invention for treating people infected with diseases and other debilitating medical conditions caused by bacterial, eukaryotic, prion, and viral pathogens and by non-pathogenic inflammation. Persons having allergic rhinitis, arthritis, bronchitis, hemorrhoids, urticaria, toothache, tinea pedis, acute viral nasopharyngitis, herpes simplex, dandruff, itching, bromhidrosis, and vaginitis have been successfully treated according to the present medicinal techniques without significant adverse side effects. The invention thereby provides a very large advance over conventional medicinal treatment techniques.

DESCRIPTION OF THE PREFERRED EMBODIMENTS

Persons afflicted with diseases and other debilitating medical conditions caused by bacterial, eukaryotic, prion, and viral pathogens, including fungal, spore-caused, and parasitic infections, and by non-pathogenic-caused inflammation are treated in accordance with the invention with a medicinal drug formed at least partially with salt, i.e., one or more individual salts, of peroxymonosulfuric acid ($H_2SO_5$). Such a salt is generally referred to as a peroxymonosulfate. The medicinal drug formed at least partially with peroxymonosulfate is referred to herein as being of type I. In accordance with the invention, the medicinal drug of type I can also be administered to persons for preventing them from contracting debilitating medical conditions caused by bacterial, eukaryotic, prion, and viral pathogens, including fungal, spore-caused, and parasitic infections, and by non-pathogenic-caused inflammation.

Peroxymonosulfates are generally strong oxidizing agents, i.e., they readily provide (or release) oxygen under certain conditions at standard temperature (20-25° C.) and standard pressure (760 ton). In particular, oxygen is readily released by a peroxymonosulfate when it is present in water, typically in aqueous solution. The active oxygen content $R_{AO}$, i.e., fraction or percentage of readily providable oxygen, of an oxidizing agent such as a peroxymonosulfate is given generally as:

$$R_{AO} = m_{AO}/m_{OXAG} = W_O N/W_{OXAG} \qquad (1)$$

where $m_{AO}$ is the mass of the active oxygen in the oxidizing agent, $m_{OXAG}$ is the mass of the oxidizing agent, $W_O$ is the molecular weight of oxygen, N is the number of moles of active oxygen in a mole of the oxidizing agent, and $W_{OXAG}$ is the molecular weight of the oxidizing agent.

Oxygen's molecular weight $W_O$ is approximately 16.00. Accordingly, active oxygen content $R_{AO}$ is more particularly given as:

$$R_{AO} \approx 16.00 N/W_{OXAG} \qquad (2)$$

The oxidizing capability of the peroxymonosulfate used in forming the medicinal drug of type I is believed to be a factor in the drug's effectiveness in combating bacterial, eukaryotic, prion, and viral pathogens that attack humans and in causing non-pathogenic-caused inflammation to be reduced in humans. Eq. 2 thus provides an estimate of the oxidizing capability of the peroxymonosulfate used in forming the drug of type I.

The peroxymonosulfates include alkali metal salts, alkaline earth metal salts, and ammonium (group) salts of peroxymonosulfuric acid. Such a peroxymonosulfate is chemically representable as $M_iH_j(SO_5)_k$ where M is an alkali metal in Group 1a of the Periodic Table, an alkaline earth metal in Group 1b of the Periodic Table, or an ammonium group and where i, j, and k are integers. Integers i, j, and k satisfy the relationship ni+j equals 2k where n is an integer equal to 1 for an alkali metal or an ammonium group and equal to 2 for an alkaline earth metal. Integer j can be 0 such that hydrogen is absent in the $H_j$ term of $M_iH_j(SO_5)_k$.

The alkali metal salts of peroxymonosulfuric acid consist of its alkali metal hydrogen salts and its dialkali metal salts. For primary alkali metals lithium, sodium, and potassium, the alkali metal salts of peroxymonosulfuric acid are lithium hydrogen peroxymonosulfate ($LiHSO_5$), dilithium peroxymonosulfate ($Li_2SO_5$), sodium hydrogen peroxymonosulfate ($NaHSO_5$), disodium peroxymonosulfate ($Na_2SO_5$), potassium hydrogen peroxymonosulfate ($KHSO_5$), and dipotassium peroxymonosulfate ($K_2SO_5$). Similar to potassium hydrogen peroxymonosulfate often referred to as potassium peroxymonosulfate, lithium hydrogen peroxymonosulfate and sodium hydrogen peroxymonosulfate may respectively be referred to simply as lithium peroxymonosulfate and sodium peroxymonosulfate.

Rubidium and cesium are additional alkali metals. To the extent manufacturable without being toxic, the alkali metal salts of peroxymonosulfuric acid further include rubidium hydrogen peroxymonosulfate ($RbHSO_5$), dirubidium peroxymonosulfate ($Rb_2SO_5$), cesium hydrogen peroxymonosulfate ($CsHSO_5$), and dicesium peroxymonosulfate ($Cs_2SO_5$). Rubidium hydrogen peroxymonosulfate and cesium hydrogen peroxymonosulfate may respectively be referred to simply as rubidium peroxymonosulfate and cesium peroxymonosulfate.

The alkaline earth metal salts of peroxymonosulfuric acid consist of its alkaline earth metal salts and its alkaline earth metal hydrogen salts. For primary alkaline earth metals magnesium and calcium, the alkaline earth metal salts of peroxymonosulfuric acid are magnesium peroxymonosulfate ($MgSO_5$), magnesium dihydrogen diperoxymonosulfate ($MgH_2(SO_5)_2$), calcium peroxymonosulfate ($CaSO_5$), and calcium dihydrogen diperoxymonosulfate ($CaH_2(SO_5)_2$).

Beryllium, barium, and strontium are additional alkaline earth metals. To the extent manufacturable without being toxic, the alkaline earth metal salts of peroxymonosulfuric acid further include beryllium peroxymonosulfate ($BeSO_5$), beryllium dihydrogen diperoxymonosulfate ($BeH_2(SO_5)_2$), barium peroxymonosulfate ($BaSO_5$), barium dihydrogen diperoxymonosulfate ($BaH_2(SO_5)_2$), strontium peroxymonosulfate ($SrSO_5$), and strontium dihydrogen diperoxymonosulfate ($SrH_2(SO_5)_2$).

An ammonium salt of peroxymonosulfuric acid is chemically representable as $NR_aR_bR_cR_dHSO_5$ or as $NR_aR_bR_cR_d$-$NR_eR_fR_gR_hSO_5$ where each of $R_a$, $R_b$, $R_c$, $R_d$, $R_e$, $R_f$, $R_g$, and $R_h$ is variously hydrogen or a hydrocarbon group such as an alkyl, cycloalkyl, aryl, or aralkyl group. For the $NR_aR_bR_cR_dNR_eR_fR_gR_hSO_5$ ammonium peroxymonosulfates, $R_e$, $R_f$, $R_g$, and $R_h$ are typically respectively the same as $R_a$, $R_b$, $R_c$, and $R_d$. The non-carbon ammonium salts of peroxymonosulfuric acid are ammonium hydrogen peroxymonosulfate ($NH_4HSO_5$) and diammonium peroxymonosulfate (($NH_4)_2SO_5$). Ammonium hydrogen peroxymonosulfate may be referred to simply as ammonium peroxymonosulfate.

Peroxymonosulfuric acid may also form salts with metals in parts of the Periodic Table other than the alkali metals of Group 1a and the alkaline earth metals of Group 1b. For instance, peroxymonosulfuric acid may form salts with metals, e.g., zinc, in Group 2b of the Periodic Table. To the extent manufacturable, the Group 2b salts of peroxymonosulfuric acid include zinc peroxymonosulfate ($ZnSO_5$) and zinc dihydrogen diperoxymonosulfate ($ZnH_2(SO_5)_2$).

The salt of peroxymonosulfuric acid used in forming the medicinal drug of type I is preferably potassium hydrogen peroxymonosulfate ($KHSO_5$). In a molecule of potassium hydrogen peroxymonosulfate, a pair of oxygen atoms singly bonded to each other are situated between the sulfur and hydrogen atoms. The single oxygen-oxygen bond readily breaks under certain conditions, e.g., when the molecule of potassium hydrogen peroxymonosulfate is dissolved in a suitable solvent such as water, to release one of the oxygen atoms involved in the single oxygen-oxygen bond. The molecular weight $W_{KHSO5}$ of potassium hydrogen peroxymonosulfate is approximately 152.17. Potassium hydrogen peroxymonosulfate has one mole of active oxygen per mole of potassium hydrogen peroxymonosulfate. Utilizing Eq. 2 given above, active oxygen content $R_{AO}$ of pure potassium hydrogen peroxymonosulfate is approximately 10.5%.

In further accordance with the invention, the potassium hydrogen peroxymonosulfate used in forming the medicinal drug of type I is normally provided as a component of a multiple salt, preferably potassium monopersulfate triple salt composition $(KHSO_5)_x(KHSO_4)_y(K_2SO_4)_z$ for which the sum of mole fractions x, y, and z equals 1. Potassium hydrogen sulfate ($KHSO_4$) and potassium sulfate ($K_2SO_4$), again sometimes referred to as dipotassium sulfate, are physically bonded to potassium hydrogen peroxymonosulfate in potassium monopersulfate triple salt composition.

Neither potassium hydrogen sulfate nor potassium sulfate readily releases oxygen under the same conditions at standard temperature and pressure for which potassium hydrogen peroxymonosulfate readily releases oxygen. The overall oxidizing agent formed with potassium monopersulfate triple salt composition normally used in forming the medicinal drug of type I thereby consists of (a) active oxygen-releasing material formed by potassium hydrogen peroxymonosulfate and (b) other material, referred to here as inactive material, consisting of potassium hydrogen sulfate and potassium sulfate.

The mass fraction $F_{mp}$ of a component $C_p$ of a general product having n components $C_1, \ldots C_q, \ldots C_n$, each being of a molecular weight $W_q$ and of a mole fraction $F_{Mq}$ in the product, is given as:

$$F_{mp} = W_p F_{Mp} \bigg/ \sum_{q=1}^{n} W_q F_{Mq} \qquad (3)$$

where q is an integer varying from 1 to n and where the sum of mole fractions $F_{M1}, \ldots F_{Mq}, \ldots F_{Mn}$ equals 1. The molecular weights $W_{K2SO5}$, $W_{KHSO4}$, and $W_{K2SO4}$ of potassium hydrogen peroxymonosulfate, potassium hydrogen sulfate, and potassium sulfate respectively are 152.17, 136.17, and 174.26 (to two significant digits beyond the decimal point). Letting $F_{mK2SO5}$, $F_{mKHSO4}$, and $F_{mK2SO4}$ represent the respective mass fractions of potassium hydrogen peroxymonosulfate, potassium hydrogen sulfate, and potassium sulfate in potassium monopersulfate triple salt composition $(KHSO_5)_x(KHSO_4)_y(K_2SO_4)_z$, mass fractions $F_{mK2SO5}$, $F_{mKHSO4}$, and $F_{mK2SO4}$ are respectively given in terms of mole fraction x of potassium hydrogen peroxymonosulfate, mole fraction y of potassium hydrogen sulfate, and mole fraction z of potassium sulfate as:

$$F_{mKHSO5} = W_{KHSO5}x/(W_{KHSO5}x + W_{KHSO4}y + W_{K2SO4}z) \quad (4)$$
$$\approx 152.17x/(152.17x + 136.17y + 174.26z)$$

$$F_{mKHSO4} = W_{KHSO4}x/(W_{KHSO5}x + W_{KHSO4}y + W_{K2SO4}z) \quad (5)$$
$$\approx 136.17x/(152.17x + 136.17y + 174.26z)$$

$$F_{mK2SO4} = W_{K2SO4}x/(W_{KHSO5}x + W_{KHSO4}y + W_{K2SO4}z) \quad (6)$$
$$\approx 174.26x/(152.17x + 136.17y + 174.26z)$$

Potassium monopersulfate triple salt composition is implemented with potassium monopersulfate triple salt ($2KHSO_5 \cdot KHSO_4 \cdot K_2SO_4$) in one formulation used in forming the medicinal drug of type I. Inasmuch as mole fractions x, y, and z respectively are 0.5, 0.25, and 0.25 in this formulation, use of Eqs. 4-6 yields the following values for mass fractions $F_{mK2SO5}$, $F_{mKHSO4}$, and $F_{mK2SO4}$ in this formulation: (a) mass fraction $F_{mK2SO5}$ of potassium hydrogen peroxymonosulfate is approximately 50%, (b) mass fraction $F_{mKHSO4}$ of potassium hydrogen sulfate is approximately 22%, and (c) mass fraction $F_{mK2SO4}$ of potassium sulfate is approximately 28%.

The active oxygen content $R_{AO}$, i.e., fraction or percentage of active oxygen, in potassium monopersulfate triple salt composition is given in terms of mole fractions x, y, and z by the relationship:

$$R_{AO} = W_O x/(W_{KHSO5}x + W_{KHSO4}y + W_{K2SO4}z) \quad (7)$$
$$\approx 16.00x/(152.17x + 136.17y + 174.26z)$$

where $W_O$ is again the molecular weight of oxygen. For the preceding formulation in which mole fractions x, y, and z respectively are 0.5, 0.25, and 0.25, active oxygen content $R_{AO}$ is approximately 5.2%.

The mole fraction $F_{Mp}$ of component $C_p$ in a general product is, in turn, given as:

$$F_{Mp} = \left(\frac{F_{mp}}{W_p}\right) / \sum_{q=1}^{n}\left(\frac{F_{mq}}{W_q}\right) \quad (8)$$

Accordingly, mole fractions x, y, and z respectively of potassium hydrogen peroxymonosulfate, potassium hydrogen sulfate, and potassium sulfate in potassium monopersulfate triple salt composition $(KHSO_5)_x(KHSO_4)_y(K_2SO_4)_z$ are respectively given in terms of mass fractions $F_{mK2SO5}$, $F_{mKHSO4}$, and $F_{mK2SO4}$ as:

$$x = \left(\frac{F_{mKHSO5}}{W_{KHSO5}}\right) / \left(\frac{F_{mKHSO5}}{W_{KHSO5}} + \frac{F_{mKHSO4}}{W_{KHSO4}} + \frac{F_{mK2SO4}}{W_{K2SO4}}\right) \quad (9)$$
$$\approx \left(\frac{F_{mKHSO5}}{152.17}\right) / \left(\frac{F_{mKHSO5}}{152.17} + \frac{F_{mKHSO4}}{136.17} + \frac{F_{mK2SO4}}{174.26}\right)$$

$$y = \left(\frac{F_{mKHSO4}}{W_{KHSO4}}\right) / \left(\frac{F_{mKHSO5}}{W_{KHSO5}} + \frac{F_{mKHSO4}}{W_{KHSO4}} + \frac{F_{mK2SO4}}{W_{K2SO4}}\right) \quad (10)$$
$$\approx \left(\frac{F_{mKHSO4}}{136.17}\right) / \left(\frac{F_{mKHSO5}}{152.17} + \frac{F_{mKHSO4}}{136.17} + \frac{F_{mK2SO4}}{174.26}\right)$$

$$z = \left(\frac{F_{mK2SO4}}{W_{K2SO4}}\right) / \left(\frac{F_{mKHSO5}}{W_{KHSO5}} + \frac{F_{mKHSO4}}{W_{KHSO4}} + \frac{F_{mK2SO4}}{W_{K2SO4}}\right) \quad (11)$$
$$\approx \left(\frac{F_{mK2SO4}}{174.26}\right) / \left(\frac{F_{mKHSO5}}{152.17} + \frac{F_{mKHSO4}}{136.17} + \frac{F_{mK2SO4}}{174.26}\right)$$

Mass fractions $F_{mKHSO5}$, $F_{mKHSO4}$, and $F_{mK2SO4}$ respectively are approximately 45%, 25%, and 30% in another formulation of potassium monopersulfate triple salt composition used in forming the medicinal drug of type I. Use of Eqs. 9-11 yields the following values for mole fractions x, y, and z in this second formulation: (a) mole fraction x of potassium hydrogen peroxymonosulfate is approximately 46%, (b) mole fraction y of potassium hydrogen sulfate is approximately 28%, and (c) mole fraction y of potassium sulfate is approximately 26%. The second formulation of the potassium monopersulfate triple salt composition is then approximately given as $(KHSO_5)_{0.46}(KHSO_4)_{0.28}(K_2SO_4)_{0.26}$ or approximately equivalently as $1.7KHSO_5 \cdot 1.1KHSO_4 \cdot K_2SO_4$.

Active oxygen content $R_{AO}$ is given in terms of mass fraction $F_{mKHSO5}$ as:

$$R_{AO} = (W_O/W_{KHSO5})F_{KHSO5} \quad (12)$$
$$\approx (16.00/152.17)F_{KHSO5}$$
$$\approx 0.1051 F_{KHSO5}$$

For the second formulation of potassium monopersulfate triple salt composition in which mass fraction $F_{mKHSO5}$ is approximately 45%, active oxygen content $R_{AO}$ is approximately 4.7%.

The medicinal drug of Type I may be formed with a small percentage, normally no more than a few percent by mass, typically no more than 1% by mass, of one or more other potassium-sulfur-oxygen salts, such as potassium persulfate ($K_2S_2O_8$), present as impurity in the potassium monopersulfate triple salt composition. Although this might cause the resultant composition of potassium hydrogen peroxymonosulfate, potassium hydrogen sulfate, potassium sulfate, and each other potassium-sulfur-oxygen salt to strictly be a multiple salt of at least four potassium-sulfur-oxygen salts, the resultant composition is substantially potassium monopersulfate triple salt composition because the impurity potassium-sulfur-oxygen salt constitutes only a small percentage by mass of the resultant composition. Furthermore, the potassium hydrogen peroxymonosulfate, potassium hydrogen sulfate, and potassium sulfate used in forming the resultant composition still constitute potassium monopersulfate triple salt composition.

The medicinal drug of type I may be formed with one or more components in addition to salt of peroxymonosulfuric acid and, when the salt of peroxymonosulfuric acid consists of potassium hydrogen peroxymonosulfate provided as a component of potassium monopersulfate triple salt composition, one or more components in addition to potassium hydrogen sulfate, potassium sulfate, and any impurity in the potassium monopersulfate triple salt composition. The components used to form the drug of type I are preferably all water soluble such that the drug of type I is water soluble. The drug of type I is, as discussed further below, typically provided in a therapeutically inactive pharmaceutically acceptable carrier, often water in which the components used to form the drug are dissolved. One or more of the components used to form the drug of type I may, nonetheless, be non-soluble in water. In that case, each non-water-soluble component is normally in liquid form or colloidally suspendable in water.

Formulations of potassium peroxymonosulfate triple salt composition suitable for use in forming the medicinal drug of type I can be manufactured in various ways. It is typically desirable that a $(KHSO_5)_x(KHSO_4)_y(K_2SO_4)_z$ formulation used in forming the drug of type I have a higher active oxygen content, and a lower potassium persulfate impurity content, than the second formulation of potassium monopersulfate triple salt composition in which mass fraction $F_{mKHSO5}$ is approximately 45%.

With reference to Martin, cited above, a suitable process for manufacturing the potassium triple salt composition entails first adding a hydrogen peroxide ($H_2O_2$) solution containing at least 70% hydrogen peroxide by mass to a sulfuric acid ($H_2SO_4$) solution containing at least 90% sulfuric acid by mass at a substoichiometric sulfuric-acid-to-hydrogen-peroxide ratio to produce a first Caro's acid solution containing peroxymonosulfuric acid and hydrogen peroxide. The first Caro's acid solution is then combined with oleum containing sulfuric acid and sulfur trioxide ($SO_3$). The oleum reacts with water in the first Caro's acid solution to produce a second Caro's acid solution. The temperature is maintained below 30°, normally below 20° C., during the preceding steps.

A potassium compound is added to the second Caro's acid solution to produce a partially neutralized solution containing potassium monopersulfate triple salt composition $(KHSO_5)_x(KHSO_4)_y(K_2SO_4)_z$. The partially neutralized solution is concentrated to form a slurry of the potassium monopersulfate triple salt composition at a desired specific gravity, e.g., 1.55-1.65. The slurry is typically formed by mixing in a vacuum evaporator at a temperature of no more than 35° C. The slurry is separated into mother liquor and solids of which the solids contain the monopersulfate triple salt composition. The solids are dried at a temperature of no more than 90° C., preferably no more than 70° C. Further details on this process are presented in Martin, the contents of which are incorporated by reference herein.

By suitably controlling the process conditions, mole fractions x, y, and z of the potassium monopersulfate triple salt composition $(KHSO_5)_x(KHSO_4)_y(K_2SO_4)_z$ fall into the following ranges. Broadly, x is 0.43-0.64, y is 0.15-0.43, and z is 0.15-0.43. More narrowly, x is 0.46-0.64, y is 0.15-0.37, and z is 0.15-0.37.

The specific values of mole fractions x, y, and z within the preceding ranges are often selected so that active oxygen content $R_{AO}$ of the resultant formulation of the potassium monopersulfate triple salt composition is greater than the approximate 4.7% active oxygen content of the second formulation of potassium monopersulfate triple salt composition in which mass fraction $F_{mKHSO5}$ of potassium hydrogen peroxymonosulfate is approximately 45% and in which corresponding mole fraction x of potassium hydrogen peroxymonosulfate is approximately 46%. For instance, mole fractions x, y, and z are typically chosen so that active oxygen content $R_{AO}$ of the formulation of the potassium monopersulfate triple salt composition is greater than 4.9%. At the same time, the amount of potassium persulfate in the formulation of the potassium monopersulfate triple salt composition is less than 0.5% by mass.

Increasing mole fraction x of potassium hydrogen peroxymonosulfate in potassium monopersulfate triple salt composition $(KHSO_5)_x(KHSO_4)_y(K_2SO_4)_z$ generally causes active oxygen content $R_{AO}$ to increase. For example, an $R_{AO}$ value of 5.2%, and thus greater than 4.7%, is achieved with the first-mentioned formulation in which mole fractions x, y, and z respectively are 0.5, 0.25, and 0.25. Active oxygen content $R_{AO}$ of potassium monopersulfate triple salt composition can be made greater than 6% by choosing mole fraction x of potassium hydrogen peroxymonosulfate to be at, or close to, the upper limit of 0.64 in the two sets of mole fraction ranges given above. As another example, use of Eq. 7 yields an $R_{AO}$ value of approximately 6.7% when mole fraction x is 0.64 and mole fractions y and z both are 0.18.

As described in Martin, the foregoing process can be modified in various ways. For instance, a suprastoichiometric sulfuric-acid-to-hydrogen-peroxide ratio can be used instead of a substoichiometric sulfuric-acid-to-hydrogen-peroxide ratio. In that case, mole fractions x, y, and z of the potassium monopersulfate triple salt composition $(KHSO_5)_x(KHSO_4)_y(K_2SO_4)_z$ fall into the further narrowed range set in which x is 0.53-0.64, y is 0.15-0.37, and z is 0.15-0.37.

When mole fraction x equals 0.53 at the lower end of the mole fraction range for potassium hydrogen peroxymonosulfate in this third set of mole fraction ranges, use of Eq. 7 yields an $R_{AO}$ value of approximately of 5.5% when mole fractions y and z both are 0.235. Since the upper limit of mole fraction x is 0.64 in this third set of mole fraction ranges, active oxygen content $R_{AO}$ of potassium monopersulfate triple salt composition can readily be chosen to be 5.5-6.8% by choosing mole fractions x, y, and z to appropriately fall into this third set of mole fraction ranges.

In accordance with the invention, people afflicted with diseases and other debilitating medical conditions caused by bacterial, eukaryotic, prion, and viral pathogens, again including fungal, spore-caused, and parasitic infections, and by non-pathogenic-caused inflammation are treated with a medicinal drug formed at least partially with water-soluble inorganic halide and an oxidizing agent reactable in water, typically aqueous solution, with the halide to generate hypohalite ions. The medicinal drug is also normally formed at least partially with (anhydrous) alkali metal phosphate and sulfamic acid. The chemical formula for sulfamic acid, alternatively known as amidosulfonic acid, amidosulfuric acid, aminosulfonic acid, and sulfamidic acid, is $H_3NSO_3$. The medicinal drug formed at least partially with the preceding four components is referred to herein as being of type II. The medicinal drug of type II can also be administered in accordance with the invention to persons for preventing them from contracting debilitating medical conditions caused by bacterial, eukaryotic, prion, and viral pathogens, including fungal, spore-caused, and parasitic infections, and by non-pathogenic-caused inflammation.

The oxidizing agent used in forming the medicinal drug of type II contains active oxygen-releasing material that readily releases oxygen under certain conditions at standard temperature and standard pressure. More particularly, oxygen is readily released by the active-oxygen-releasing material when it is present in water, typically in aqueous solution. The oxidizing agent typically may include additional oxygen-containing material, referred to here as inactive material, which does not readily release oxygen under the same conditions at standard temperature and pressure for which the active oxygen-releasing material readily releases oxygen.

The ratio of the mole fraction $F_{MHI}$ of the inorganic halide to the mole fraction $F_{MAORM}$ of the active oxygen-releasing material in the medicinal drug of type II is normally 0.01-4, preferably 0.02-2, more preferably 0.03-1, even more preferably 0.04-0.5, typically 0.06-0.18. The ratio of the mole fraction $F_{MAMP}$ of the alkali metal phosphate to mole fraction $F_{MAORM}$ of the active oxygen-releasing material in the drug of type II is normally 0.04-40, preferably 0.1-5, more preferably 0.2-1, typically 0.4. The ratio of the mole fraction $F_{MSA}$ of sulfamic acid to mole fraction $F_{MAORM}$ of the active oxygen-releasing material in the drug of type II is normally 0.03-30, preferably 0.1-10, more preferably 0.2-1, typically 0.35-0.7.

The inorganic halide is normally sodium chloride (NaCl), an alkali metal halide. The inorganic halide can alternatively or additionally include one or more other alkali metal halides, one or more alkaline earth metal halides, or/and one or more ammonium halides. In particular, the inorganic halide can alternatively or additionally include one or more of lithium fluoride (LiF), sodium fluoride (NaF), potassium fluoride (KF), rubidium fluoride (RbF), cesium fluoride (CsF), beryllium fluoride ($BeF_2$), magnesium fluoride ($MgF_2$), calcium fluoride ($CaF_2$), strontium fluoride ($SrF_2$), barium fluoride ($BaF_2$), ammonium fluoride ($NH_4F$), lithium chloride (LiCl), potassium chloride (KCl), rubidium chloride (RbCl), cesium chloride (CsCl), beryllium chloride ($BeCl_2$), magnesium chloride ($MgCl_2$), calcium chloride ($CaCl_2$), strontium chloride ($SrCl_2$), barium chloride ($BaCl_2$), ammonium chloride ($NH_4Cl$), lithium bromide (LiBr), sodium bromide (NaBr), potassium bromide (KBr), rubidium bromide (RbBr), cesium bromide (CsBr), beryllium bromide ($BeBr_2$), magnesium bromide ($MgBr_2$), calcium bromide ($CaBr_2$), strontium bromide ($SrBr_2$), barium bromide ($BaBr_2$), ammonium bromide ($NH_4Br$), lithium iodide (LiI), sodium iodide (NaI), potassium iodide (KI), rubidium iodide (RbI), cesium iodide (CsI), beryllium iodide ($BeI_2$), magnesium iodide ($MgI_2$), calcium iodide ($CaI_2$), strontium iodide ($SrI_2$), barium iodide ($BaI_2$), and ammonium iodide ($NH_4I$) provided that such other halide does not react with the alkali metal phosphate to form an insoluble salt.

The alkali metal phosphate is normally one or more of sodium metaphosphate ($(NaPO_3)_n$), monosodium phosphate ($NaH_2PO_4$), disodium phosphate ($Na_2HPO_4$), trisodium phosphate ($Na_3PO_4$), tetrasodium pyrophosphate ($Na_4P_2O_7$), potassium metaphosphate ($(KPO_3)_n$), monopotassium phosphate ($KH_2PO_4$), dipotassium phosphate ($K_2HPO_4$), tripotassium phosphate ($K_3PO_4$), and tetrapotassium pyrophosphate ($K_4P_2O_7$). For each of sodium metaphosphate and potassium metaphosphate, n is a plural integer, i.e., n is 2 or more. Sodium metaphosphate can, for example, be implemented with sodium hexametaphosphate ($(NaPO_3)_6$) or/and sodium trimetaphosphate ($(NaPO_3)_3$). Potassium metaphosphate can similarly be implemented with potassium hexametaphosphate ($(KPO_3)_6$) or/and potassium trimetaphosphate ($(KPO_3)_3$).

The material used to form the medicinal drug of type II may include a non-reducing organic acid, normally malic acid ($HO_2CCH_2CHOHCO_2H$) or succinic acid ($HO_2CCH_2CH_2CO_2H$). The ratio of the mole fraction $F_{MNROA}$ of the non-reducing organic acid to mole fraction $F_{MAORM}$ of the active oxygen-releasing material in the drug of type II is normally 0.01-50, preferably 0.05-5, more preferably 0.1-1, typically 0.25.

The material used to form medicinal drug of type II may also include a surfactant, typically sodium dodecylbenzene sulfonate ($NaC_{18}H_{29}SO_3$). Other candidates for the surfactant are lauryl ether sulfates, ethylene oxide/propylene oxide alkyl phenol condensates, polyglycol ethers of fatty alcohols, fatty acid ethylene oxide condensates, polyglycol ethers of aklyn phenols, and fatty alcohol ethoxylates. The ratio of the mole fraction $F_{MSF}$ of the surfactant to mole fraction $F_{MAORM}$ of the active oxygen-releasing material in the drug of type II is normally 0.03-30, preferably 0.05-10, more preferably 0.1-10, typically 0.3.

The medicinal drug of type II is, as discussed further below, often provided in a therapeutically inactive pharmaceutically acceptable liquid carrier, normally water. Each of the components, including the oxidizing agent, of the material used to form the drug of type II is then soluble, e.g., water soluble, in the carrier, colloidably suspendable in the carrier, or in liquid form so as to be miscible or emulsible with the carrier. The components used to form the drug of type II are preferably all water soluble such that the drug of type II is water soluble.

The active-oxygen-releasing material in the oxidizing agent for the medicinal drug of type II normally includes persulfate or/and peroxyphthalate. Persulfate candidates for the active-oxygen-releasing material include peroxymonosulfates (having $SO_5^{-2}$ groups) and peroxydisulfates (having $S_2O_8^{-2}$ groups). The active-oxygen-releasing material preferably includes peroxymonosulfate, i.e., salt of peroxymonosulfuric acid, such as alkali metal salt, alkaline-earth metal salt, or/and ammonium salt of peroxymonosulfuric acid. More preferably, the salt of peroxymonosulfuric acid includes potassium hydrogen peroxymonosulfate.

Other sulfur-containing candidates for the active-oxygen-releasing material in the oxidizing agent for the medicinal drug of type II include thiosulfates (having $S_2O_3^{-2}$ groups). A peroxyphthalate candidate for the active-oxygen-releasing material is potassium monoperoxyphthalate. The active-oxygen-releasing material can alternatively or additionally be implemented with chlorine-oxygen-containing compounds such as hypochlorites (having $ClO^-$ groups), chlorites (having $ClO_2^-$ groups), chlorates (having $ClO_3^-$ groups), and perchlorates (having $ClO_4^-$ groups).

To the extent not mentioned above, candidates for the active-oxygen-releasing material in the oxidizing agent for the medicinal drug of type II include oxygen-releasing salts such as, alkali metal salts (particularly potassium, sodium, and lithium salts), alkaline earth metal salts (particularly calcium and magnesium salts), and ammonium salts of other inorganic and organic acids. Other candidates for the active-oxygen-releasing material are the alkali metal and ammonium salts of permanganic acid ($HMnO_4$), especially potassium permanganate ($KMnO_4$) but also potentially lithium permanganate ($LiMnO_4$), sodium permanganate ($NaMnO_4$), rubidium permanganate ($RuMnO_4$), cesium permanganate ($CsMnO_4$), and ammonium permanganate ($NH_4MnO_4$). Insofar as the drug of type II is provided in a therapeutically inactive pharmaceutically acceptable liquid carrier, again normally water, all of these candidates for the active-oxygen-releasing material need to be soluble, e.g., water soluble, in the carrier, colloidably suspendable in the carrier, or in liquid form so as to be miscible or emulsible with the carrier.

When the active-oxygen-releasing material consists at least partially of salt of peroxymonosulfuric acid such as potassium hydrogen peroxymonosulfate, the medicinal drug of type II implements the medicinal drug of type I for the situation in which the drug of type I is formed with salt of peroxymonosulfuric acid and one or more other components aside from material closely bonded to the salt of peroxymonosulfuric acid. More particularly, when the salt of peroxymonosulfuric acid consists of potassium hydrogen peroxymonosulfate provided as a component of potassium monopersulfate triple salt composition, the drug of type II implements the drug of type I for the situation in which the drug of type I is formed with potassium hydrogen peroxymonosulfate and one or more components other than the potassium hydrogen sulfate and the potassium sulfate in potassium monopersulfate triple salt composition. All of the preceding comments about the drug of type I then apply to the drug of type II. The composite drug of types I and II is referred to here as the medicinal drug of "type I/II".

The medicinal drug of type I/II is preferably formed with potassium hydrogen peroxymonosulfate as the active oxygen-releasing material, sodium chloride as the inorganic halide, sodium hexametaphosphate as the alkali metal phosphate, sulfamic acid, malic acid as the non-reducing organic acid, and sodium dodecylbenzene sulfonate as the surfactant. The potassium hydrogen peroxymonosulfate in this formulation is normally provided as a component of potassium monopersulfate triple salt composition. The mass fractions of potassium hydrogen peroxymonosulfate, potassium hydrogen sulfate, and potassium sulfate in potassium monopersulfate triple salt composition $(KHSO_5)_x (KHSO_4)_y (K_2SO_4)_z$ are approximately 45%, 25%, and 30% in this formulation so that mole fractions x, y, and z are respectively approximately 46%, 28%, and 26%.

As mentioned above, neither potassium hydrogen sulfate nor potassium sulfate readily releases oxygen under the same conditions at standard temperature and pressure for which potassium hydrogen peroxymonosulfate readily releases oxygen. Consequently, the potassium hydrogen sulfate and potassium sulfate in potassium monopersulfate triple salt composition of potassium monopersulfate triple salt composition constitute inactive material of the material used to form the preceding preferred formulation of the medicinal drug of type I/II.

The number $M_p$ of moles of each component $C_p$ used in forming a multi-component product consisting of a total of $M_T$ moles is:

$$M_p = F_{Mp} M_T \qquad (13)$$

where $F_{Mp}$ again is the mole fraction of component $C_p$ and where the sum of all mole fractions $F_{Mp}$ again equals 1. The molar ratio $R_{Mb/a}$ is the ratio of the number $M_b$ of moles of a component $C_b$ in the product to the number $M_a$ of moles of a component $C_b$ in the product. Using Eq. 13, molar ratio $R_{Mb/a}$ is:

$$R_{Mb/a} = F_{Mb}/F_{Ma} \qquad (14)$$

The parameter $F_{Mb}/F_{Ma}$ is the mole fraction ratio $R_{FMb}/a$, i.e., the ratio of the mole fraction $F_{Mb}$ of component $C_b$ in the product to the mole fraction $F_{Ma}$ of component Ca in the product. Hence, mole fraction ratio $R_{FMb/a}$ equals molar ratio $R_{Mb/a}$.

Using Eq. 8, mole fraction ratio $R_{FMb/a}$ and molar ratio $R_{Mb/a}$ are given as:

$$R_{FMb/a} = R_{Mb/a} = \left(\frac{F_{mb}}{F_{ma}}\right)\left(\frac{W_a}{W_b}\right) \qquad (15)$$

where $F_{ma}$ and $F_{mb}$ are the respective mass fractions of components $C_a$ and $C_b$ in the product and $W_a$ and $W_b$ are the respective molecular weights of components $C_a$ and $C_b$. Consequently, the ratio $R_{mb/a}$ of the mass fraction (or mass percentage) $F_{mb}$ of component $C_b$ to the mass fraction (or mass percentage) $F_{ma}$ of component $C_a$ is:

$$R_{mb/a} = \frac{F_{mb}}{F_{ma}} = R_{FMb/a}\left(\frac{W_b}{W_a}\right) = R_{Mb/a}\left(\frac{W_b}{W_a}\right) \qquad (16)$$

Eq. 16 can be employed to convert mole fraction (or molar) ratios into mass fraction ratios and thus into mass fractions.

Potassium hydrogen peroxymonosulfate as the active oxygen-releasing material, sodium chloride as the inorganic halide, sodium hexametaphosphate as the alkali metal phosphate, sulfamic acid, malic acid as the non-reducing organic acid, and sodium dodecylbenzene sulfonate as the surfactant are present at the following mass percentages of the overall material used to form the preceding preferred formulation of the medicinal drug of type I/II:

a. Potassium hydrogen peroxymonosulfate—normally 2-95%, preferably 6-90%, more preferably 10-60%, typically 20-25%;
b. Sodium chloride—normally 0.001-30%, preferably 0.005-7.5%, more preferably 0.01-5%, typically 0.5-1.5%;
c. Sodium hexametaphosphate—normally 2-60%, preferably 5-45%, more preferably 10-30%, typically 18%;
d. Sulfamic acid—normally 1-30%, preferably 1.5-15%, more preferably 3-10%, typically 5-10%;
e. Malic acid—normally 0.1-40%, preferably 0.5-30%, more preferably 1-20%, typically 5-10%; and
f. sodium dodecylbenzene sulfonate—normally 1-50%, preferably 7.5-37.5%, more preferably 10-25%, typically 15%.

The remainder of the material used to form this formulation of the medicinal drug of type I/II largely consists of the potassium hydrogen sulfate and the potassium sulfate in the potassium monopersulfate triple salt composition that provides the potassium hydrogen peroxymonosulfate.

The medicinal drug of type I or II (including the medicinal drug of type I/II) may be provided in solid, semiliquid, or liquid form. The term "semiliquid" refers here to matter having properties between a solid and a liquid. The viscosity of semiliquid matter is sufficiently high that the semiliquid matter, when placed on a surface, flows slowly and does not rapidly adopt the shape of the underlying surface. This contrasts to liquid matter which, when placed on a surface, readily flows and rapidly adopts the shape of the underlying surface, typically within a few seconds for up to a kilogram of the liquid, and to solid matter which does not flow.

Solid (dry) forms of the drug of type I or II are powders and tablets (pills) which disintegrate in the body when taken orally. When the drug of type I or II is provided in solid form, the drug itself is in solid form and is normally dispersed largely throughout a therapeutically inactive pharmaceutically acceptable solid carrier. Powder implementations of the drug of type I or II may be enclosed in water-soluble capsules (small closed containers such as jackets, sachets, films, and the like) which disintegrate in the body when taken orally. Coating agents (such as sugar, gelatin, hydroxypropyl cellulose, and hydroxypropylmethyl cellulose phthalate) may be variously provided in one or more layers or films on the tablets and capsules. The tablets and capsules can be structured to provide metered-release forms of the drug of type I or II.

The following materials can be variously admixed into solid powder and tablet forms of the medicinal drug of type I or II: vehicles (such as lactose, mannitol, glucose, microcrystalline cellulose, and starch) which help deliver the drug ingredients, binders (such as hydroxypropyl cellulose, polyvinylpyrrolidone, magnesium metasilicate aluminate, sodium stearate, polyoxyethylene and mixtures thereof), lubricants (such as magnesium stearate, polyethylene glycol, and sodium benzoate), stabilizing agents, solution adjuvants (such as glutamic acid and aspartic acid), water-absorbable materials (such as fumed silica, sodium carbonate, magnesium carbonate, and potassium carbonate) for reducing moisture, and effervescents (such as cellulose calcium glycolate, bicarbonate, carbonate, sodium bicarbonate, sodium carbonate, and citric, adipic, and tartaric acids or other similar organic acids) for releasing carbon dioxide to assist with effervescence in causing the solid drug material to disintegrate. Carbon dioxide and sodium bicarbonate may also assist in therapeutic activity. Additionally, dyes, other coloring agents, flavoring agents, fragrances, corrosion inhibitors, activity indicators, and organic activators can be applied to the solid forms of the drug of type I or II.

Semiliquid forms of the medicinal drug of type I or II include gels, creams, pastes, and ointments. When the drug of type I or II is provided in semiliquid form, the drug is normally dispersed throughout a therapeutically inactive pharmaceutically acceptable semiliquid carrier. Although the carrier is semiliquid, the drug of type I or II can itself be solid, semiliquid, or even liquid if the drug is a suitable small mass percentage of the carrier. In a typical semiliquid form of the drug of type I or II, the drug itself consists of solid particles. The semiliquid drug of type I or II may be provided with various additives such as wetting agents, emulsifying agents, dyes, other coloring agents, flavoring agents, fragrances, corrosion inhibitors, activity indicators, organic activators, stabilizers, and buffering agents.

Liquid forms of the medicinal drug of type I or II include solutions, suspensions, lotions, emulsions, liniments, syrups, elixirs, and tinctures. In some cases, the dividing line between liquid and semiliquid forms of the drug of type I or II is unclear. When the drug of type I or II is provided in liquid form, the drug is typically dispersed throughout a therapeutically inactive pharmaceutically acceptable liquid carrier. Similar to semiliquid forms of the drug of type I or II, the drug itself can be solid, semiliquid, or liquid form. In a typical liquid form of the drug of type I or II, the drug itself consists of solid particles dissolved or colloidably suspended in the carrier. The liquid carrier is normally water (purified and/or distilled) but can be ethanol or a mixture of ethanol and water. The liquid drug of type I or II may be provided with additives such as wetting agents, suspending agents, emulsifying agents, dyes, other coloring agents, flavoring agents, fragrances, corrosion inhibitors, activity indicators, organic activators, stabilizing agents (such as sodium sulfate), and buffering agents.

As discussed further below, liquid forms of the medicinal drug of type I or II can be administered by injection or spraying. In addition to water or/and ethanol, the liquid carrier for drug injection may include one or more of vegetable oil, propylene glycol, polyethylene glycol, solution adjuvants (such as glutamic acid and aspartic acid), and soothing agents. The liquid carrier for drug spraying may include isotonic buffers (such as sodium chloride, sodium citrate, and citric acid).

The peroxymonosulfate used in forming the medicinal drug of type I can be combined with any other component of the drug and with a therapeutically inactive pharmaceutically acceptable carrier for the drug according to various techniques. The oxidizing agent, preferably peroxymonosulfate, used in forming the medicinal drug of type II can similarly be combined with the other components of the drug and with a therapeutically inactive pharmaceutically acceptable carrier for the drug according to various techniques. In the following description of such combining techniques for the medicinal drugs of types I and II, the term "peroxymonosulfate material" for the drug of type I means both the peroxymonosulfate, when it is provided as substantially a single salt, and a multiple salt composition, such as potassium monopersulfate triple salt composition for potassium hydrogen peroxymonosulfate, which contains the peroxymonosulfate as a component. The term "oxidizing agent material" for the drug of type II means both (a) the active oxygen-releasing material when the oxidizing agent is provided as substantially a single material and (b) a multi-material composition which contains the active oxygen-releasing material as a component. When the oxidizing agent consists substantially solely of peroxymonosulfate, the peroxymonosulfate material is the oxidizing agent material.

In one drug formation technique, the carrier, the peroxymonosulfate material, and any other component of the medicinal drug of type I are initially provided in solid particulate form. This technique is applicable to the medicinal drug of type II in a variation in which the carrier, the oxidizing agent material, and the other components of the drug are initially provided in solid particulate form. The particles for both the drug of type I and the drug of type II are mixed together to form a powdery substance. The mixing is normally performed so that the particles of the drug are distributed largely uniformly the particles of the carrier. The drug of type I or II is then available for use as a powder. If desired, the powder can be inserted into water-soluble capsules.

If the medicinal drug of type I or II is to be in solid tablet form, the powdery substance is suitably processed to create solid tablets, including tablets that provide metered-release forms of the drug after it is administered. The processing may include providing the tablets with suitable coatings.

Largely the same procedure can be followed if the medicinal drug of type I or II is to be provided in a therapeutically inactive pharmaceutically acceptable semiliquid carrier such as a cream, gel, or ointment except that the powdery substance is suitable processed to form the semiliquid carrier with the drug particles distributed throughout it. Alternatively, the carrier can initially be provided in semiliquid form with the drug of type I or II furnished in solid particulate form. If the drug of type I contains at least one component besides the peroxymonosulfate material, the particles of the drug components are mixed together. Since the drug of type II has multiple components, its components are simply mixed together. The particles of the drug of type I or II are then mixed into the carrier. The mixing for the drug of type I or II is normally performed so that the drug particles are distributed largely uniformly throughout the semiliquid material of the carrier.

In a further drug formation technique where the carrier is to be a liquid and where the medicinal drug of type I is to be formed with at least one component besides the peroxymonosulfate material, the components of the drug are provided in solid particulate form. This technique is applicable to the medicinal drug of type II in a variation in which the oxidizing agent material and other components of the drug are initially provided in solid particulate form. The particles of the components of the drug of type I or II are mixed together to form the drug of type I or II as a powdery substance. The powdery drug is then combined with the liquid carrier in such a manner as to be distributed throughout the carrier.

The carrier is again a liquid in yet another drug formation technique. The peroxymonosulfate material for the medicinal drug of type I is provided in solid particulate form and is mixed into the liquid carrier. If the drug of type I is to be formed with at least one component besides the peroxymonosulfate material, each additional component is provided in solid particulate form or in liquid form. Each additional component for the drug of type I is then mixed into the liquid carrier separate from the peroxymonosulfate material. This technique is applicable to the medicinal drug of type II in a variation in which the oxidizing agent material is again initially provided in solid particulate form and in which each other component of the drug is initially provided in solid particulate form or in liquid form. Each additional component for the drug of type II is mixed into the liquid carrier separate from the oxidizing agent material. The mixing for the drug of type I or II is performed so that the particles of the drug of type I or II are distributed throughout the carrier.

When the carrier is a liquid, the particles of the peroxymonosulfate material and any other drug component provided in particulate form for the medicinal drug of type I preferably dissolve in the carrier to form a solution and are thereby distributed substantially uniformly throughout the carrier. For the medicinal drug of type II, each drug component provided in particulate form preferably dissolves in the carrier to form a solution and thus is distributed substantially uniformly throughout the carrier.

Alternatively, the particles of the peroxymonosulfate material and any other drug component provided in particulate form for the medicinal drug of type I can be suspended in the carrier to form a colloid or emulsion. As necessary, the colloid or emulsion is suitably mixed so that the particles of the peroxymonosulfate material and any other drug component provided in particulate form are distributed substantially uniformly throughout the carrier. For the medicinal drug of type II, each drug component provided in particulate form can similarly be suspended in the carrier to form a colloid or emulsion. As necessary, the colloid or emulsion is likewise suitably mixed so that the particles of the oxidizing agent material and each other drug component provided in particulate form are distributed substantially uniformly throughout the carrier.

In some of the techniques for combining the peroxymonosulfate material and at least one other component of the medicinal drug of type I with the carrier, the peroxymonosulfate may react with another drug component, typically in the carrier. If the drug of type I is to be formed with at least two components besides the peroxymonosulfate material, two or more of these other components may react with one another, again typically in the carrier. The peroxymonosulfate or/and any other drug component besides the peroxymonosulfate material may even react with the carrier. The possibility of such reaction(s) is greater when the carrier is a liquid such as water. As a result, the chemical structure of the final constituents of the drug of type I may differ from the chemical structure of the components used to form the drug. Nonetheless, the drug of type I can reasonably be described as being "formed" with the peroxymonosulfate material and each other indicated component and thus as being "formed" at least partially with the peroxymonosulfate.

As indicated above, the oxidizing agent for the medicinal drug of type II is reactable in water, typically aqueous solution, with the halide to generate hypohalite ions. The chemical formula for a hypohalite is XOH (or HOX) where X represents a halogen such as fluorine, chlorine, bromine or iodine. A hypohalite ion thus has the chemical formula $XO^-$. When the therapeutically inactive pharmaceutically acceptable carrier is a water-containing liquid and when the oxidizing agent and the halide are dissolved in the water or are suspended in colloidal form in the water, hypohalite ions are thereby produced by reaction of the oxidizing agent with the halide. Consequently, the chemical structures of some of the components of the drug of type II in the water-containing carrier differ from the chemical structures of the corresponding components used to form the drug of type II. However, the reaction does not normally cause any significant precipitation of hypohalite material, modified oxidizing agent material, or any other material. The drug of type II can reasonably be described as being "formed" with the inorganic halide, sulfamic acid, alkali metal phosphate, and the oxidizing agent, and when used, the organic acid and the surfactant.

The medicinal drug of types I and II is administered in various ways to people afflicted with diseases and other debilitating medical conditions caused by bacterial, eukaryotic, prion, and viral pathogens, including fungal, spore-caused, and parasitic infections, and by non-pathogenic-caused inflammation. In general, the drug of type I or II can be administered to a person by any procedure or/and route which enables the drug to reach the particular location(s) afflicted with the disease to be alleviated by the drug. Depending on various factor including the nature of the disease, the administration technique can be global, i.e., systemic, or local and thus targeted at the diseased location(s).

A topical technique is often used to administer the medicinal drug of type I or II. As used herein, topical administration generally means bringing the drug of type I or II into contact with the outer surface, typically the skin, of the human body and not by introducing the drug into the human body via one or more major openings, i.e., openings other than pores, naturally present along the outer surface of the human body or/and one or more openings artificially formed along the outer surface of the human body. Topical administration can be performed by manually bringing the drug of type I or II into contact with the body, by spraying, by immersion (bath or soak), and by other techniques which physically bring the drug into contact with the body. The drug of type I or II can be in solid powder form, semiliquid form, or liquid form during topical administration. Topical administration of the drug of type I or II on an eye, typically with the drug in liquid form, can be performed by spraying the drug into the eye, vaporizing the drug into the eye, or/and with eye drops.

The medicinal drugs of types I and II can also be administered non-topically. Non-topical administration, the converse of topical administration, generally here means introducing the drug of type I or II into the human body via one or more major openings naturally present along the outer surface of the human body or/and one or more openings artificially formed along the outer surface of the human body. Non-topical techniques for administering the drug of type I or II include oral administration, intranasal administration, intraotical administration, vaginal administration, rectal administration, urethral administration, and injection alternatively referred to as infusion or parenteral administration.

Oral administration is normally done with the medicinal drug of type I or II in solid tablet, capsule, or powder form but can be done with the drug in liquid form and sometimes with the drug in semiliquid form. The tablets, capsules, and powders may provide metered release of the drug of type I or II. For oral administration of the drug of the drug of type I or II in liquid or semiliquid form, the drug can also be placed in the mouth without having the drug go substantially through the esophagus to the stomach. For instance, a liquid form of the drug of type I or II can be administered orally by spraying the drug into the mouth or by placing the drug in the mouth and then gargling.

Intranasal administration in which the medicinal drug of type I or II enters at least one of the nostrils is typically done with the drug of type I or II in liquid form. Intranasal administration of the drug of type I or II can be performed by inhalation into a nostril, spraying into a nostril, vaporizing the drug into a nostril, with nose drops, or/and by other techniques which physically bring the drug into contact with the inside of a nostril.

Intraotic administration can done with the medicinal drug of type I or II in solid powder form, semiliquid form, and liquid form. In intraotic administration of the drug of type I or II, the drug typically enters the ear canal. Intraotic administration of the drug of type I or II into the ear canal can be performed by manually bringing the drug into contact with the ear canal, by spraying into the ear canal, with ear drops, vaporizing the drug into the ear canal, by immersion, or/and by other techniques which physically bring the drug into contact with the ear canal. Spraying can be done with nebulizers to achieve selected dosages. Intraotic administration of the drug of type I or II also includes introducing the drug into the middle ear or/and the inner ear and thus past the eardrum.

Vaginal and rectal administration can done with the medicinal drug of type I or II in solid powder form, semiliquid form, and liquid form. Urethral administration is typically done with the drug of type I or II in liquid form. Pessaries, suppositories, enemas and the like can be variously employed in vaginal, rectal, and urethral administration of the drug of type I or II.

Administration by injection is typically done with the medicinal drug of type I or II in liquid form. Types of injection administration of the drug of type I or II include intravenous, intramuscular, subcutaneous, intracardiac, intracavernosal, intradermal, intraosseous, intraperitoneal, and intrathecal injection.

The concentration of the medicinal drug of type I or II in its solid, semiliquid, or liquid carrier is normally 0.00001-5%, preferably 0.001-3%, more preferably, 0.1-2%, typically 0.5-1%, by mass. These ranges are particularly applicable to the medicinal drug of type I/II for which the active oxygen-releasing material in the oxidizing agent for the drug of type II consists substantially of peroxymonosulfate, preferably potassium hydrogen peroxymonosulfate, used in forming the drug of type I and for which the material used in forming the drug of type I or II includes inorganic halide, alkali metal phosphate, and sulfamic acid. The specific concentration is chosen to be therapeutically effective and non-toxic when administered in the ways described above.

The time during which the medicinal drug of type I or II is in contact with the area under treatment, especially for topical administration of the drug, varies depending upon the selected route of administration, the desired therapeutic effect, and the particular disease or other debilitating medical condition being treated with the drug. The time of contact for a liquid form of the drug of type I or II is normally 1 minute-12 hours, preferably 1 minute-6 hours, more preferably 1 minute-2 hours, typically 1-30 minutes. The time of contact for a semiliquid form of the drug of type I or II is normally 1 minute-12 hours, preferably 1 minute-6 hours, more preferably 1 minute-2 hours, typically 30 minutes-1 hour. The time of contact for a solid form of the drug of type I or II is normally 1 minute-12 hours, preferably 1 minute-6 hours, more preferably 1 minute-2 hours, typically 30 minutes-1 hour. The preceding times of contact for liquid, semiliquid, and solid forms of the drug of types I and II apply to continuous administration of the drug. The time-of-contact of the drug of type I or II can be combined with metered-release forms of the drug to obtain desired therapeutic effects.

The range of administered dosages of the medicinal drug of type I or II varies depending upon the selected route of administration, the recipient's characteristics, including age, body weight, general state of health, desired therapeutic effect, the duration of the treatment, and the disease or other debilitating medical condition being treated with the drug. The drug of type I or II can, for example, be separately administered normally 1-12 times per day, preferably 1-8 times per day, more preferably 1-6 times per day, typically 1-4 times per day, at selected unit dosages or continuously administered for selected periods at selected rates by suitable continuous administration techniques, such as intravenous injection, to achieve selected total dosage amounts. Unit dosages can be combined with metered-release dosages to obtain desired therapeutic effects.

The medicinal drug of type I or II can be administered more than 12 times daily depending on the nature of the particular disease or other debilitating medical condition being treated with the drug. The concentration of the drug of type I or II in its solid, semiliquid, or liquid carrier may exceed 5% by mass in some cases. The total administered amount and administration schedule is selected so that the drug of type I or II is therapeutically effective in alleviating the symptoms of the disease or other debilitating medical condition while being non-toxic or otherwise injurious to the recipient. Additionally, the drug of type I or II may be used with many other medicines and therapies.

The time period during which a person is treated with the medicinal drug of type I or II varies depending upon the desired therapeutic effect, the particular disease or other debilitating medical condition being treated with the drug, and the person's characteristics, including age, body weight, and general state of health. The treatment period is chosen to be therapeutically effective in alleviating the symptoms of the disease being treated while avoiding toxicity difficulties with the drug of type I or II. The treatment period with the drug of type I or II is normally 1 day-12 months, preferably 1 day-6 months, more preferably 1 day-3 months, and typically 1-30 days. Nonetheless, the treatment can extend over multiple years.

The treatment plan for the medicinal drug of type I or II can be a one-time treatment, daily treatments, weekly treatments, monthly treatments, yearly treatments, or/and a long term treatment plan. Depending on the severity of the debilitating condition of the person being treated with the drug of type I or II, the treatment plan varies widely as shown by the examples presented below. Treatment with the drug of type I or II can be used as a preventative measure or/and infrequently to maintain a healthy lifestyle.

The medicinal drug of type I or II is particularly useful in treating allergic rhinitis, arthritis, bronchitis, hemorrhoids, urticaria, toothache, tinea pedis, acute viral nasopharyngitis, herpes simplex, dandruff, itching, bromhidrosis, and vaginitis. The types of arthritis include osteoarthritis and gouty arthritis. The drug of type I or II may be used to treat many other diseases and otherwise debilitating medical conditions. Other uses of the drug of type I or II include uses as an analgesic for treating pain and headaches, as an antipyretic for treating fever, as a detoxifying agent for treating hypersensitivity to various drug or/and body reactions, as a cutaneous agent for treating debilitating skin conditions, as an hematologic for treating blood diseases and other cardiac conditions, as a treatment for genetic or hereditary disorders, as a palliate for reducing conditions, as an idiopathic for treating unknown causes of a condition, and as an antidote for preventing or counteracting poisons and other such toxic conditions.

Given below are examples of using the medicinal drug of type I/II for treating allergic rhinitis, osteoarthritis, gouty arthritis, bronchitis, hemorrhoids, urticaria, toothache, tinea pedis, acute viral nasopharyngitis, herpes simplex, dandruff, itching, bromhidrosis, and vaginitis. The formulation of the drug of type I/II used in these examples was the preferred formulation, mentioned above, in which the drug was formed with potassium hydrogen peroxymonosulfate as the active oxygen-releasing material, sodium chloride as the inorganic halide, sodium hexametaphosphate as the alkali metal phosphate, sulfamic acid, malic acid as the non-reducing organic acid, and sodium dodecylbenzene sulfonate as the surfactant at approximately the typical mass percentages mentioned above. A formulation approximating this formulation is commercially available in the product Virkon. This formulation of the drug of type I/II is referred to below as the "Medicine".

The Medicine for each person infected with allergic rhinitis, osteoarthritis, gouty arthritis, bronchitis, hemorrhoids, urticaria, toothache, tinea pedis, acute viral nasopharyngitis, herpes simplex, dandruff, itching, bromhidrosis, and vaginitis is provided for topical, intranasal, oral, or/and injection administration 1-12 times per day, preferably 1-8 times per day, more preferably 1-6 times per day, typically 1-4 times per day, in liquid form at a dosage of 0.00001-5%, preferably 0.001-3%, more preferably 0.1-2%, typically 0.5-1%, for a time of contact of 1 minute-12 hours, preferably 1 minute-6 hours, more preferably 1 minute-2 hours, typically 1-30 minutes . The treatment period in each in each of the following examples is normally 1-12 months, preferably 1-6 months, more preferably 1-3 months, typically 1-30 days.

EXAMPLE 1

Allergic Rhinitis

A teenage female had allergic rhinitis. The female stated that she experienced annual episodes of itching, burning, congestion, and watering of mucosal membranes apparently resulting from hypersensitivity to plant allergens. The Medicine was provided to the female as a 1% solution for intranasal administration by spraying into the nostrils 3 times a day at 4-hour intervals for 2 weeks. The female reported that her allergic rhinitis symptoms were relieved after 3 days and that the symptoms virtually disappeared after 10 days. The female then stopped using the Medicine. The female reported that the allergy symptoms returned after 14 more days, that she resumed taking the Medicine, and that the symptoms disappeared within several more days. As a preventative measure, the female reports that she now uses the Medicine before hay fever season.

EXAMPLE 2

Allergic Rhinitis

An adult male had allergic rhinitis for 15 years. The Medicine was provided to the male as a 0.5% solution for intranasal administration by spraying into the nostrils 4 times a day at 3-hour intervals for 5 days. After 5 days of use, the male reported that the allergic rhinitis symptoms virtually went away and that he no longer had to blow his nose throughout the day.

Example 3

Allergic Rhinitis

An adult male had severe allergic rhinitis for 20 years apparently from sensitivity to chemical irritants. The male had virtually all the normal symptoms of allergic rhinitis throughout the week except that, on weekends, the allergy irritation reportedly wasn't as strong apparently due to the avoidance of chemical irritants. The male reported that he had tried many antihistamines, corticosteroids, and herbs for treating the allergic rhinitis but to no avail. The Medicine was provided to the male as a 1% solution for intranasal administration by spraying into the nostrils 4 times a day at 4-hours intervals for 7 days. The male reported that the allergic rhinitis was greatly alleviated by day 5, that he had never previously used a product as efficient as the Medicine for alleviating allergic rhinitis, and that, starting on day 8, he did not need to blow his nose anymore.

EXAMPLE 4

Allergic Rhinitis

An adult female had allergic rhinitis apparently due to her cat. The female reported that she had sought many allergic rhinitis treatments and remedies, including high efficiency particulate air filters throughout her house, keeping her cat away from her personal bedroom, and consistently cleaning and vacuuming her home, without success. The Medicine was provided to the female as a 1% solution for intranasal administration by spraying into the nostrils 3 times a day at 4-hour intervals for 7 days. On day 8, the female reported that her allergic rhinitis symptoms were greatly alleviated and that the Medicine was the best product she has ever tried for alleviating her allergic rhinitis. The female reports that she now uses the Medicine three times a week to maintain a non-allergenic lifestyle.

EXAMPLE 5

Allergic Rhinitis

An adult female had allergic rhinitis for 20-25 years. The symptoms included extreme congestion and itchy/runny nose apparently from weather changes due to constant travels. The female reported that she had previously attempted, without success, to treat her allergic rhinitis with many different types of herbs. The Medicine was provided to the female as a 1% solution for intranasal administration by spraying into the nostrils 3 times a day at 4-hour intervals for 7 days. The female reported that that her allergic rhinitis symptoms were virtually gone on day 5 and that the Medicine was the best product she has ever used for allergic rhinitis. The female reports that she now uses the Medicine whenever she feels there may be an onset of allergic rhinitis and that she never travels without the Medicine.

EXAMPLE 6

Osteoarthritis

A retired adult male had osteoarthritis for 10 years. The male stated that he was in constant pain throughout the day, thereby limiting his life substantially to his surroundings. The male reported that he had tried many treatments, such as NSAIDs, glucosamine, and glucocorticoids, for his osteoarthritis without effective relief. The Medicine was provided to the male as a 1% solution for topical administration via complete-body immersion (bath) for 15 minutes, with morning and night applications, for a minimum of 2 weeks. The male reported that, after 7 days of treatment, the pain was relieved greatly and that, after 14 days of treatment, the pain was very minimal. The male reports that he now uses the Medicine at least twice a week to reduce pain of osteoarthritis.

EXAMPLE 7

Osteoarthritis

A retired adult female had osteoarthritis. She stated that she had aching pain in her joints, mainly in her hands, for the past 6 months. The female reported that she had attempted, without success, to treat her osteoarthritis via the daily use of vitamins. The Medicine was provided to the female as a 1% solution for topical administration by immersing her hands in the solution for 10 minutes once a day for 7 days. The female reported that, on day 5, the aching, particularly at night, had gone away.

EXAMPLE 8

Osteoarthritis

An adult male laborer had osteoarthritis, apparently from doing heavy lifting throughout the day. The Medicine was provided to the male as a 0.5% solution for topical administration via complete-body immersion (bath) for 15 minutes once a day for a few days until he felt better. The male reported that, after 3 days of use, the pain and aching in his knees and hands significantly lessened with no side effects. The male reports that the treatment has made his muscles feel extremely relaxed and that that he now uses the Medicine once a week as a treatment and a preventative.

EXAMPLE 9

Gouty Arthritis

A retired adult male had gouty arthritis for 10 years. The male reported that he was in excruciating pain on random days and that previously attempted treatments for the pain were unsuccessful. The Medicine was provided to the male as a 1% solution for topical administration via complete-body immersion once a day, before bedtime, for a minimum of 20 minutes for 7 days. The male reported that the pain was greatly relieved on day 4. The male reports that that he now sleeps better than in many previous years and that he continues to use the Medicine at least twice a week as a treatment and preventative.

EXAMPLE 10

Gouty Arthritis

A retired adult male had gouty arthritis for 15 years. The male stated that he had severe pain throughout the day, that he had chalky white material on his skin, and that he experienced constipation. The male reported that he had tried ibuprofen to treat the gouty arthritis with no significant success. The Medicine was provided to the male as a 1% solution for topical administration via complete-body immersion for 10 minutes, before bedtime, for 10 days. After 4 days, the male reported that the pain subsided by over 50%, that he had not felt this comfortable for the past 15 years, and that the chalky material had disappeared from his skin. On day 10, the male reported that the severe pain was virtually gone, that he had regular bowel movements, and that he no longer experienced constipation.

EXAMPLE 11

Gouty Arthritis

An adult male had gouty arthritis for 10 years. The male stated that he often felt pain and swelling in his joints during those 10 years. The male reported that he had tried treatments such as ibuprofen, colchicines, and intra-glucocorticoids for the osteoarthritis without significant success. The Medicine was provided to the male as a 1% solution for topical administration via complete-body immersion for 10 minutes a day and for 7 days. After 7 days, the male reported that the pain and swelling had decreased drastically. The male reports that he is now sleeping better than any time that he can remember.

EXAMPLE 12

Bronchitis

An adult female had severe coughing and sputum due to bronchitis. The female reported that the bronchitis had been intermittent for 10 years and that she had tried many treatments for her bronchitis and consumed substantial amounts of water daily with no success. The Medicine was provided to the female as a 0.1% solution for oral administration by spraying into the mouth 3 times per day at 4-hour intervals for 7 days. After the 7 days, the female reported that her bronchitis was greatly alleviated, that the urge to cough had diminished greatly, and that the sputum was virtually gone. The female reports that she now feels better than she has in the past 10 years.

EXAMPLE 13

Bronchitis

A teenage female had bronchitis. The female reported that she coughed throughout the day but could find movements that minimize the coughing when she was in school. The female reported that she had tried treatments such as cough suppressants, particularly codeine, for the bronchitis with little success. The Medicine was provided to the female as a 0.1% solution for oral administration by spraying into the mouth 2 times a day, morning and night, for 1 week. After 5 days, the female reported that the coughing and associated pains had greatly diminished. The female reported that she continued treatment with the Medicine for another 10 days. At the end of those 10 days, the female reported that her cough had virtually away. The female reports that she has not had a recurrence of bronchitis since the treatment.

EXAMPLE 14

Bronchitis

An adult female had bronchitis. The female complained of endless nights of coughing and that the resultant lack of sleep caused her to be tired on work days. The female reported that she had tried herbs and cough suppressants to reduce the coughing. The female also reported that those treatments sometimes helped reduce the coughing and attendant phlegm but that the pain of coughing remained. The Medicine was provided to the female as a 0.1% solution for oral administration by spraying into the mouth 3 times a day at 4-hour intervals for 7 days. The female reported that, on day 4, the coughing and attendant pain were greatly reduced and that the phlegm had disappeared. The female also reports that she now has less tiresome days.

EXAMPLE 15

Hemorrhoids

An adult female had hemorrhoids for over 5 years. The female stated that the hemorrhoids were so severe as to prevent her from working, that she was confined to bed during most of each day due to severe pain in walking and standing, and that the pain was almost unbearable during bowel movements. The Medicine was provided to the female as a 1% solution for rectal/topical administration 1-2 times a day for 14 days. For the rectal/topical administration, the female was instructed to perform bowel movements in a container filled with the Medicine to a level so that her buttocks were completely immersed in the Medicine, so that the Medicine contacted the outer layer of the anus, and so that the Medicine moved through the anus into the rectum. After each bowel movement, the Medicine in the container was to be discarded. The female reported that her hemorrhoids were greatly alleviated and that she was now able to walk far distances which she had not been able to do for over 5 years.

EXAMPLE 16

Hemorrhoids

An adult male had hemorrhoids for almost 20 years. The male reported that he was able to functionally largely normally throughout those years but that he incurred excessive bleeding during bowel movements. The Medicine was provided to the male as a 1% solution for rectal/topical administration 1-2 times a day for 7 days. For the rectal/topical administration, the male was instructed to perform bowel movements in a container filled with the Medicine to a level so that his buttocks were completely immersed in the Medicine, so that the Medicine contacted the outer layer of the anus, and so that the Medicine moved through the anus into the rectum. After each bowel movement, the Medicine in the container was to be discarded. After 7 days, the male reported that the excessive bleeding was virtually gone. The male reports that he now uses the Medicine whenever bleeding occurs during bowel movements.

EXAMPLE 17

Hemorrhoids

An adult male had external hemorrhoids for about 5 years. The male stated that he would forcibly push the external hemorrhoid back inside the rectum with his finger after bowel movements and that he would then be able to function normally and even play sports. The Medicine was provided to the male as a 1% solution for rectal/topical administration once or twice a day for several weeks. For the rectal/topical administration, the male was instructed to perform bowel movements in a container filled with the Medicine to a level so that his buttocks were completely immersed in the Medicine, so that the Medicine contacted the outer layer of the anus, and so that the Medicine moved through the anus into the rectum. After each bowel movement, the Medicine in the container was to be discarded. The male reported that he used the Medicine once a day for 25 days. On day 26, the male reported that the external hemorrhoid intruded back inside the rectum with no manual force after a bowel movement.

EXAMPLE 18

Hemorrhoids

An adult female had hemorrhoids occasionally for 5 years. The Medicine was provided to the female as a 1% solution for rectal/topical administration once or twice a day at an occurrence of hemorrhoids. For the rectal/topical administration, the female was instructed to perform bowel movements in a container filled with the Medicine to a level so that her buttocks were completely immersed in the Medicine, so that the Medicine contacted the outer layer of the anus, and so that the Medicine moved through the anus into the rectum. After each bowel movement, the Medicine in the container was to be discarded. The female reports that, upon an occurrence of hemorrhoids, she performs this treatment for about 2 days and the symptoms of hemorrhoids disappear.

EXAMPLE 19

Urticaria

An adult female had a severe outbreak of urticaria apparently due to consumption of raw seafood. The female stated that she had itchy and bumpy red spots on her face, back and thighs. The female stated that she had tried many treatments for her urticaria. The Medicine was provided to the female as a 0.5% solution for topical administration via complete-body immersion for 20 minutes once a day for a few days. The female reported that the itchiness was relieved on the night of initial treatment and that her urticaria was virtually gone on day 3. The female also reported that no previous treatment for her urticaria was as fast acting as the Medicine.

EXAMPLE 20

Urticaria

A teenage female had a severe outbreak of urticaria apparently due to an allergic reaction to an injection. The female stated that her body and face were virtually completely covered with red skin welts. The Medicine was provided to the female as a 1% solution for topical administration via complete-body immersion for 10 minutes. The female reported that the symptoms or urticaria virtually disappeared after 1 treatment.

EXAMPLE 21

Urticaria

An adult female had an outbreak of urticaria for unknown reasons. The female stated that she had itchy and bumpy red skin mainly on her thighs, her back, and most noticeably her face. The Medicine was provided to the female as a 1% solution for topical administration via complete-body immersion for 10 minutes a day for a few days subsequent to two days of no treatment of any kind for the urticaria. The female reported that the symptoms of urticaria virtually disappeared after 3 days of treatment with the Medicine.

EXAMPLE 22

Toothache

An adult female had a tooth extracted and was in extreme pain due to the tooth extraction. The Medicine was provided to the female as a 1% solution for oral administration by gargling for 1 minute. The female reported that the pain diminished greatly in about 30 minutes. The female further reported that she continued using the Medicine before bedtime that night and the next day during the morning and evening and that, after 2 days of treatment, the toothache pain disappeared.

EXAMPLE 23

Toothache

A teenage female had 3 wisdom teeth extracted and was in pain due to the tooth extraction with saliva dripping out of her mouth and some bleeding. The female stated that she used hydrocodone for the pain. The Medicine was provided to the female as a 1% solution for oral administration by gargling for 30 seconds at 1-hour intervals 2 times a day on the first day. The female reported that the bleeding subsided after the second treatment with the Medicine on the first day. The female reported that she used the Medicine on the second day and that the amount of saliva dripping out of her mouth was greatly reduced after 30 minutes of treatment with the Medicine on the second day. The female further reported that she used the Medicine once a day for the next 2 days with no significant saliva dripping.

EXAMPLE 24 toothache

A teenage male had 3 teeth extracted on the same day. The male stated that, subsequent to the tooth extraction, he felt no pain due to the tooth extraction and had minimal bleeding but had saliva dripping out of his mouth. The Medicine was provided to the male as a 1% solution oral administration by gargling for 30 seconds at 4-hour intervals for a few days. The male reported that the saliva dripping was greatly reduced after the first day and that virtually no saliva dripping occurred at the end of the second day.

EXAMPLE 25

Tinea Pedis

An adult male had tinea pedis with itching, cracking, and burning lesions of his toes. The Medicine was provided to the male as a 1% solution for topical administration via foot immersion for 10 minutes a day for several days. The male reported that his toes were healed after 5 days and that the Medicine was one of the most effective medications that he had ever used.

EXAMPLE 26

Tinea Pedis

An adult male had chronic tinea pedis. The Medicine was provided to the male as a 0.5% solution for topical administration via foot immersion for 10 minutes a day for at least several days. In 7 days, the male reported that his tinea pedis had greatly diminished. In approximately 7 more days, the male reported that the tinea pedis had virtually disappeared.

EXAMPLE 27

Tinea Pedis

An adult male reported excessive flaking on his feet and severe itching in between his toes apparently due to tinea pedis. The Medicine was provided to the male as a 1% solution for topical administration via foot immersion for 10 minutes a day for at least several days. On day 2, the male reported that the severe itching had subsided but that flakes were still present. After two weeks of daily treatment with the Medicine, the male reported that the flaking had subsided.

EXAMPLE 28

Acute Viral Nasopharyngitis

An adult female apparently had viral nasopharyngitis. She reported the typical viral nasopharyngitis symptoms of sneezing, congestion, and fatigue. The Medicine was provided to the female as a 0.1% solution (i) for intranasal administration by spraying and (ii) for oral administration by spraying, each type of administration to be performed 3 times a day at 4-hour intervals for 4 days. The female reported that the symptoms of sneezing, congestion, and restlessness had significantly decreased by day 4 and that they had virtually disappeared on the morning of day 5.

EXAMPLE 29

Acute Viral Nasopharyngitis

An adult female reported that she contracted acute viral nasopharyngitis at least 3 times a year. The Medicine was provided to the female as a 1% solution (i) for intranasal administration by spraying and (ii) for oral administration by swallowing one tablespoon of the Medicine, each type of administration to be performed 3 times a day at 4-hour intervals as a preventative when she sensed the onset of acute viral nasopharyngitis and during acute viral nasopharyngitis. On a day that the female sensed the onset of acute viral nasopharyngitis, the female reported that she started administering the Medicine to herself in the foregoing manner. The female reported that she had the acute viral nasopharyngitis symptoms of itchy throat, sneezing, and runny nose on the next day. The female further reported that she continued administering the Medicine to herself in the foregoing manner for another 3 days at which time all the acute viral nasopharyngitis symptoms disappeared.

EXAMPLE 30

Acute Viral Nasopharyngitis

An adult female reported that she contracted acute viral nasopharyngitis symptoms during the winter for 20 years. The female reported that she had tried many treatments, including analgesics (paracetamol), nasal decongestants (pseudoephedrine), antihistamines, and zinc preparations, for acute viral nasopharyngitis with little success. The Medicine was provided to the female as a 1% solution for intranasal administration by spraying 3 times a day at 4-hour intervals for 5 days as a preventative when she sensed the onset of acute viral nasopharyngitis and during acute viral nasopharyngitis. The female reported that she started administering the Medicine to herself in the foregoing manner on a day that she sensed the onset of acute viral nasopharyngitis, that she then experienced the symptoms of acute viral nasopharyngitis, that she continued administering the Medicine to herself in the foregoing manner for 4 more days, and that the acute viral nasopharyngitis symptoms virtually disappeared at the end of the 5 days.

EXAMPLE 31

Acute Viral Nasopharyngitis

An adult female reported that she occasionally contracted acute viral nasopharyngitis. The Medicine was provided to the female as a 1% solution (i) for intranasal administration by spraying and (ii) for oral administration by swallowing one tablespoon of the Medicine, each type of administration to be performed twice a day at 3-hour intervals as a preventative when she sensed the onset of acute viral nasopharyngitis and during acute viral nasopharyngitis. The female reported that she contracted acute viral nasopharyngitis, that she tried zinc preparations and herbal remedies for 2 days with no relief, and that she then started administering the Medicine to herself in the foregoing manner. The female further reported that her runny nose symptom of acute viral nasopharyngitis disappeared on the night of day 2 and that she continued administering the Medicine to herself in the foregoing manner for 3 more days at which time the symptoms of acute viral nasopharyngitis were virtually gone.

EXAMPLE 32

Acute Viral Nasopharyngitis

An adult female reported that she had contracted acute viral nasopharyngitis 2 days earlier. The female reported that she had continuous runny nose, congestion, itchiness, and fatigue and that she had not taken any treatment(s) for acute viral nasopharyngitis during those 2 days. The Medicine was provided to the female as a 1% solution (i) for topical administration via complete-body immersion for 10 minutes a day for 2 days and (ii) for intranasal administration by spraying at 6-hour intervals for 4 days. The female reported that her symptoms of acute viral nasopharyngitis went away in 6 days and that she had never recovered from acute viral nasopharyngitis in such a small amount of time. The female further reports that she now has the Medicine on hand as a preventative for acute viral nasopharyngitis.

EXAMPLE 33 herpes simplex

An adult female had herpes simplex in the form of herpes labialis as indicated by cold sores around her mouth. The female reported that she contracted the cold sores about 3 times a year, that she felt some pain and itching from the cold sores, and that the external visibility of the cold sores made her reluctant to meet people. The female further reported the she had tried analgesics and herbal remedies to treat the cold sores without complete success and that she normally ended up waiting about 7 days for the cold sores to scab over. The Medicine was provided to the female as a 1% solution for topical administration around the mouth at 3-hour intervals 4 times a day for 7 days. The female reported that, on day 2, the cold sores had become completely flat with the pain and itchiness substantially gone and that the cold sores were barely visible on day 6.

EXAMPLE 34

Herpes Simplex

A teenage female had herpes simplex in the form of herpes labialis as indicated by cold sores around her mouth. The female reported she contracted the cold sores 3-5 times a year, that her main concern was itching caused by the cold sores, and that she was extremely uncomfortable in scratching the cold sores due to resultant scarring. The female reported that she had tried many treatments for herpes labialis but had no success. The Medicine was provided to the female as a 1% solution for topical administration around the mouth at 4-hour intervals for 5 days. The female reported that she administered the Medicine to herself in the foregoing manner at an occurrence of herpes labialis, that the itching subsided on the first day and was gone on the second day, and that she continued to administer the Medicine to herself in the foregoing manner for another 9 days at which time the herpes labialis had seemingly disappeared. The female reports that she expects to use the Medicine at any future occurrence of herpes labialis.

EXAMPLE 35

Herpes Simplex

An adult male had herpes simplex in the form of herpes labialis as indicated by cold sores around his mouth. The male reported that he had contracted the cold sores about twice a year for 10 years, that he mostly felt bumps and minor pain around his mouth, and that the cold sores distracted his work. The male further reported that he had tried herbal remedies for treating the cold sores but had not yet found a cure for them. The Medicine was provided to the male as a 1% solution for topical administration around the mouth at 3-hour intervals 4 times a day for 7 days. The male reported that he felt no pain around the mouth after 2 days and that the cold sores were not visible after 8 more days.

EXAMPLE 36

Herpes Simplex

An adult male had herpes simplex in the form of herpes labialis as indicated by cold sores inside his mouth. The male reported that he felt no pain but did feel uncomfortable lumps in his mouth. The male also reported that he had previously contracted cold sores, that he had used vitamins to treat those cold sores, and that the vitamins did cause the cold sores to diminish but that diminishment occurred very slowly. The Medicine was provided to the male as a 1% solution for oral administration by gargling for 30 seconds at 4-hour intervals 3 times a day for 7 days. The male reported that, on day 2, the lumps in his mouth were flat and that the cold sores were barely visible on day 7.

EXAMPLE 37

Dandruff

An adult female had dandruff for about 20 years. The female stated that she avoided wearing black clothes due to the dandruff flaking and that the dandruff caused her to have low self esteem. The female reported that she had tried numerous treatments, such as zinc pyrithione, ketoconazole, selenium sulfide, and many types of herbs, to eliminate her dandruff and that (some of) these treatments did cause the amount of dandruff to decrease but that dandruff was still visible on her scalp. The Medicine was provided to the female as a 1% solution for topical administration by scrubbing the Medicine into her scalp and hair for 5 minutes and then washing her scalp and hair. The female reported that she administered the Medicine to herself in the foregoing manner 4 times a week for 2 weeks. After the 2 weeks, the female reported that the dandruff disappeared. The female reports that the dandruff has not come back.

EXAMPLE 38

Dandruff

An adult male had dandruff for about 20 years. The male stated that he tried to minimize the visibility of dandruff with hair products such as gel, hair spray, and mousse. The male further reported that he had tried many treatments to eliminate his dandruff and that (some of) these treatments did cause the amount of dandruff to decrease but that he still had substantial dandruff. The Medicine was provided to the male as a 1% solution for topical administration once a day for 2 weeks by scrubbing the Medicine into his scalp and hair for several minutes and then washing his scalp and hair. The male reported an approximate 90% reduction in the amount of dandruff in 10 days and that the dandruff was gone after the 2 weeks. Three months later, the male further reported that his dandruff had not returned.

EXAMPLE 39

Dandruff

An adult male had dandruff for 15 years. The male stated that he would wear a hat throughout the day to hide his dandruff. The male reported that he had tried many treatments to eliminate his dandruff without significant success. The Medicine was provided to the male as a 1% solution for topical administration once a day for 10 days by scrubbing the Medicine into his scalp and hair for several minutes and then washing his scalp and hair. The male reported that his dandruff was gone after the 10 days. The male reports that he no longer wears his hat.

EXAMPLE 40

Dandruff

An adult female had dandruff for 5 years. The female's dandruff was highly visible on her scalp. The female stated that she avoided wearing black clothes due to the dandruff. The female reported that she had tried many treatments to eliminate her dandruff with no success. The Medicine was provided to the female as a 1% solution for topical administration in the morning and in the evening for 2 weeks by scrubbing the Medicine into her scalp and hair for 5 minutes and then washing her scalp and hair. The female reported that, on day 10, the amount of her dandruff had decreased approximately 50%. The female further reported that she used the Medicine for another 10 days at which time her dandruff was gone.

EXAMPLE 41

Itching

An adult male had extreme itching for 5 years. The male reported that he had tried many treatments for the itching without success. The Medicine was provided to the male as a 1% solution for topical administration via complete-body immersion for 20 minutes 2 times a day for 2 weeks. The male reported that the itching had diminished by at least 50% on day 3 and that the itching was substantially gone at the end of the 2 weeks. The male reports that he now uses the Medicine twice a week as an itch preventative.

EXAMPLE 42

Itching

An adult male had itching throughout his body. The male stated that the itching was less at night than in the daytime. The male reported that he had tried many treatments, such as hydrocortisone, anti-histamines, and herbs, for the itching but without success. The Medicine was provided to the male as a 1% solution for topical administration via complete-body immersion for 10 minutes a day for 2 weeks. The male reported that he used the Medicine 3 times a week for 2 weeks and that the itching was substantially gone at the end of the 2 weeks. The male reports that he now uses the Medicine at an onset of the itching.

EXAMPLE 43

Itching

An adult male reported that he had red patches on his neck and back at birth, that the red patches began to itch as he reached middle age, and that he rubbed the red patches but did not scratch them for fear of tearing his skin. The male further reported that he had tried hydrocortisone and anti-histamines to treat the itching but had little success. The Medicine was provided to the male as a 1% solution for topical administration 3 times a day at 4-hour intervals for 2 weeks. The male reported that the itching was greatly reduced on day 5 and gone on day 10. The male reports that he now uses the Medicine once or twice a day for 2 days at an onset of the itching and that the itching then goes away.

EXAMPLE 44

Bromhidrosis

An adult male had bromhidrosis in the form of strong foot odor. The male reported that he tried treatments such as cologne and deodorant for the bromhidrosis but that these treatments caused his skin to swell and redden. The Medicine was provided to the male as a 1% solution for topical administration via foot bath immersion for 10 minutes in the morning and evening for 7 days. After 5 days, the male reported that his foot odor had disappeared. The male further reported that the foot odor returned about 30 days later, that he then used the Medicine twice in 2 days, and that the foot odor again went away.

EXAMPLE 45

Bromhidrosis

An adult male had bromhidrosis in the form of moisture and strong odor around his anus throughout the day. The male reported that he treated the bromhidrosis by rubbing with wet paper towels around the anal area to remove the odor and then rubbing with dry paper towels around the anus to remove the moisture. The male also reported that he used soap and heavy scrubbing around the anus during bathing to treat the bromhidrosis. The male reported that these treatments did cause the bromhidrosis to diminish but that the bromhidrosis returned shortly afterwards. The Medicine was provided to the male as a 1% solution for rectal/topical administration at 3-hour intervals 4 times a day for 2 weeks. The male reported that the moisture and odor were greatly reduced on day 7 and that the moisture and odor were gone at the end of the two weeks.

EXAMPLE 46

Bromhidrosis

An adult woman had bromhidrosis in the form of heavy odor around her vagina. The woman reported that she tried to treat the bromhidrosis with soap and some scrubbing around the vagina but that she used this treatment so often that the area around her vagina became swollen with a rash. The Medicine was provided to the woman as a 1% solution for vaginal/topical administration via vaginal immersion for 10 minutes a day for 2 weeks. The woman reported that the vaginal odor had greatly diminished after 3 days and that the vaginal odor was virtually eliminated after 7 days. The female reports that she has not had an occurrence of bromhidrosis since the treatment with the Medicine.

EXAMPLE 47

Bromhidrosis

An adult male had bromhidrosis in the form of strong body odor. The male reported that he had tried many treatments, including bathing and scrubbing with soap every day, changing his diet, and using deodorant and cologne, for the bromhidrosis. The male stated that he used deodorant and cologne so much that their fragrances caused him to have headaches throughout the day. The Medicine was provided to the male as a 1% solution for topical administration via complete-body immersion for 10 minutes a day and for 10 days. The male reported that his body odor was eliminated in 7 days.

EXAMPLE 48

Vaginitis

An adult female had vaginitis for 3 years. The female reported vaginitis symptoms of inflammation, burning, itching, and swelling after intercourse. The female reported that she has tried many treatments, such as topical antibiotics, anti-fungal creams, and hydrocortisone, for the vaginitis but without significant success. The Medicine was provided to the female as a 1% solution for vaginal/topical administration via vaginal immersion for 10 minutes in the morning and evening for 2 weeks. The female reported that the burning and itching in the vaginal area were significantly reduced on day 2 and that the burning, itching and inflammation in the vaginal area were greatly alleviated on day 10. The female further reports that she continues to use the Medicine after intercourse.

EXAMPLE 49

Vaginitis

An adult female had vaginitis for 6 months. The female reported that all treatments which she had tried for the vaginitis had failed except that soaking the vaginal area in hot water reduced the pain of vaginal itchiness somewhat. The Medicine was provided to the female as a 1% solution for vaginal/topical administration via vaginal immersion 15 minutes a day for 10 days. The female reported that the vaginal itchiness and associated vaginal inflammation were substantially reduced after day 2 and that the vaginitis symptoms were gone after day 10. The female reports that she has not had an occurrence of vaginitis since the treatment with the Medicine.

EXAMPLE 50

Vaginitis

An adult female had vaginitis for 2 years. The female stated that she had extreme rashes, inflammation, and itchiness in her vaginal area and had a whitish-gray discharge, often with a curd-like appearance, from the vagina. The female also stated that she experienced burning sensations throughout the day, causing her to perspire considerably. The female reported that she has tried numerous treatments, such as antihistamines, antibacterial creams, antifungal creams, hydrocortisone, and many different types of herbs, for the vaginitis but to no avail. The Medicine was provided to the female as a 1% solution for vaginal/topical administration via vaginal immersion for 15 minutes in the morning and evening for 2 weeks. The female reported that the inflammation and itchiness were greatly reduced on day 3, that the discharge disappeared on day 5, and that all her vaginitis symptoms were virtually gone at the end of the 2 weeks. After three months without vaginitis symptoms, the female reported that the inflammation and itchiness then slowly started to return. The female reported that she resumed administering the Medicine to herself and that the vaginitis rapidly went away.

While the invention has been described with reference to preferred embodiments, this description is solely for the purpose of illustration and is not to be construed as limiting the scope of the invention claimed below. For instance, the above-mentioned oxidizing agents which release oxygen may be replaced, in forming variations of some embodiments of the medicinal drug of type II, with oxidizing agents which do not release oxygen but which accept electrons in reduction-oxidization chemical reactions at oxidizing strength roughly equivalent to the oxidizing agents which release oxygen. The techniques of the invention can be used to treat non-human animals variously inflicted with diseases and other debilitating medical conditions caused by bacterial, eukaryotic, prion, and viral pathogens, including fungal, spore, and parasitic pathogens, and non-pathogenic inflammation. The techniques of the invention can be used to prevent non-human animals from contracting such debilitating medical conditions.

In addition to successfully treating, and preventing the occurrence of, allergic rhinitis, arthritis, bronchitis, hemorrhoids, urticaria, toothache, tinea pedis, acute viral nasopharyngitis, herpes simplex, dandruff, itching, bromhidrosis, and vaginitis in humans, the techniques of the invention can be used to treat or/and prevent many other debilitating human health conditions. Such other debilitating human health conditions may, for example, include medical conditions dealing with (a) the circulatory and cardiovascular system involved in pumping and circulating blood through the body in its organs and tissues, including blood vessels, arteries, capillaries, heart, and veins, (b) the digestive or gastrointestinal system involved in the ingestion and digestion of food with or through the salivary glands, esophagus, stomach, liver, gallbladder, pancreas, appendix, intestines, rectum, and anus, (c) the endocrine system which chemically controls various functions of cells, tissues, and organs through the secretion of hormones made by endocrine glands, such as the hypothalamus, pituitary, pineal, thyroid, parathyroid, and adrenal gland as well as the islets of Langerhans, ovaries, pancreas, and testes, (d) the integumentary system consisting of the skin and its related structures, the hair, nails, sweat glands, and sebaceous glands, (e) the endocannabinoid system in which the neuromodulatory lipids and receptors involve a variety of physiological processes of the brain, including appetite, cognition, emotional responses, homeostasis, motor learning, pain sensation, and synaptic plasticity, (f) the immune system which neutralizes pathogenic organisms or/and foreign matter and which includes organs such as the skin and mucous membranes, adenoids, antibody producers, leukocytes, lymph nodes, and lymphoid tissue (as in the gastrointestinal tract and bone marrow), lymphocytes including B cells and T cells, stem cells, spleen, thymus, and tonsils, (g) the lymphatic system which is involved in the circulation of lymph between the cells, tissues, and organs to the blood stream and which includes tonsils, thymus, spleen, lymph, lymph nodes, lymphatic vessels, lymphocytes, sinuses through which lymph is carried, lymphoid tissues, and bone marrow where stem cells differentiate into precursors of B cells and T cells, and (h) the muscular system formed with muscle cells and tissues that brings about movement of organs, other body parts, maintenance of posture, and heat production. The muscular system includes three basic kinds of muscles, namely (h1) the cardiac muscles which form the walls of the heart, (h2) the smooth muscles which are found in the internal organs and assist in the involuntary movements that occur in the circulatory, digestive, excretory, reproductive, and respiratory systems, and (h3) the skeletal muscles which are attached to the bones and enable voluntary movement of limbs.

Such other debilitating human health conditions may, for example, further include medical conditions dealing with (i) the musculoskeletal system in which the skeleton, muscles, bones, cartilage, joints, ligaments, tendons, and associated tissues provide movements to the body and maintain its structural form, (j) the nervous system in which the bodily system of cells, neurons, tissues, and organs regulates (collects, transfers, and processes) the body's function to internal and external stimuli and transmits impulses to the effector organs and also regulates secretions of the endocrine system by the action of neurohormones and which includes the brain, spinal cord, peripheral and autonomic nerves, nerves, ganglia, parts of the receptor organs, parts of the effector organs, and the sensory organs such as the ears and eyes, (k) the reproductive system in which organs and parts that function in reproduction in the female include ovaries, fallopian tubes, uterus, cervix, vagina, vulva, and mammary glands and in the male include seminal vesicles, prostate, urethra, vas deferens, testes, and penis, (l) the respiratory system which is involved in the intake and exchange of oxygen and carbon dioxide between the body and the environment and which includes the nose, nasal passages, pharynx, larynx, trachea, bronchi, heart, ribs, diaphragm, and lungs, (m) the skeletal system formed with bones, cartilage, joints, tendons, and other connective tissues which protect and support the body tissues and internal organs and produce blood cells and stores minerals, (n) the urinary system which is formed with the kidneys, ureters, bladder, and urethra of the urinary tract and which is involved in the regulation of water content and electrolyte concentration through the excretion of metabolic wastes, excess water, and electrolytes in the form of urine, and (o) the vestibular system which is involved with the equilibrium and organs mediating the labyrinthine sense and which includes the anterior canal, utricle, saccule, nerve, cochlea, horizontal canal, and posterior canal.

More specifically, the techniques of the invention may be used to treat or/and prevent (i) bronchial asthma, (ii) tuberculosis, (iii) cholera, (iv) syphilis, (v) meningitis, (vi) pneumonia, (vii) sepsis, (viii) cystic fibrosis, (ix) *aspergillosis,* (x) psoriasis, (xi) *aspergilloma,* (xii) amoebiasis, (xiii) Lyme disease, (xiv) malaria, (xv) prion infectious diseases including transmissible spongiform encephalopathic diseases such as Creutzfeldt-Jakob disease, Gerstmann-Sträussler-Scheinker syndrome, fatal familial insomnia, and kuru, (xvi) Alpers' syndrome, (xvii) AIDS, (xviii) hepatitides including hepatitis A, hepatitis B, hepatitis C, hepatitis D, and hepatitis E, (xix) cancers including carcinoma, sarcoma, leukemia, lymphoma, germ cell tumors, and blastic tumors, (xx) heart diseases and conditions including arrhythmias, cardiomyopathies, cardiovascular diseases, congenital heart defects, heart infections, and valvular heart diseases, (xxi) hypercholesterolemia, (xxii) hypertriglyceridemia, (xxiii) atherosclerosis, (xxiv) diabetes mellitus including diabetes type 1, diabetes type 2, gestational diabetes, congenital diabetes, cystic fibrosis-related diabetes, steroid diabetes, and forms of monogenic diabetes, (xxv) ocular disorders including conjunctivitis, trachoma, and uveitis, (xxvi) ear disorders including Ménière's disease, tinnitus, and otitis media, and (xxvii) urethral disorders including urethral stricture and urethritis.

The techniques of the invention may be used to treat or/and prevent virally caused debilitating human medical conditions arising, for example, from: (i) double-stranded DNA viruses including caudovirales, herpesvirales, ascoviridae, adenoviridae, asfarviridae, baculoviridae, coccolithoviridae, corticoviridae, fuselloviridae, guttaviridae, iridoviridae, lipothrixviridae, mimiviridae, nimaviridae, papillomaviridae, phycodnaviridae, plasmaviridae, polyomaviridae, poxviridae, rudiviridae, tectiviridae, ampullavirus, nudivirus, salterprovirus, sputnik virophage, and rhizidiovirus, (ii) single-stranded DNA viruses including the bacteriophage families inoviridae and microviridae and anelloviridae, circoviridae, geminiviridae, nanoviridae, and parvoviridae, (iii) double-stranded RNA viruses including, birnaviridae, cystoviridae, hypoviridae, partitiviridae, reoviridae, and totiviridae, (iv) positive-sense single-stranded RNA viruses including nidovirales, picornavirales, tymovirales, astroviridae, barnaviridae, bromoviridae, caliciviridae, closteroviridae, flaviviridae, leviviridae, luteoviridae, narnaviridae, nodaviridae, potyviridae, tetraviridae, togaviridae, tombusviridae, benyvirus, furovirus, hepevirus, hordeivirus, idaeovirus, ourmiavirus, pecluvirus, pomovirus, sobemovirus, tobamovirus, tobravirus, and umbravirus, (v) negative-sense single-stranded RNA viruses including mononegavirales, arenaviridae, bunyaviridae, orthomyxoviridae, deltavirus, nyavirus, ophiovirus, tenuivirus, and varicosavirus, (vi) single-stranded RNA reverse-transcription viruses including retroviruses, and (vii) double-stranded DNA reverse-transcription viruses including hepadnaviridae.

The techniques of the invention may be used to treat or/and prevent bacterially caused debilitating human medical conditions arising, for example, from: (i) gram positive bacteria with no outer membrane including actinobacteria, firmicutes, and tenericutes, (ii) gram negative bacteria with outer membrane including aquificae, bacteroidetes, chlamydiae, chlorobi, deinococcus-thermus, fusobacteria, gemmatimonadetes, nitrospirae, proteobacteria, spirochaetes, synergistetes, and verrucomicrobia, and (iii) acidobacteria, chloroflexi, chrysiogenetes, cyanobacteria, deferribacteres, dictyoglomi, fibrobacteres, planctomycetes, thermodesulfobacteria, and thermotogae.

The techniques of the invention may be used to treat or/and prevent fungal caused debilitating human medical conditions arising, for example, from blastocladiomycota, chytridiomycota, glomeromycota, microsporidia, neocallimastigomycota, dikarya, zygomycota, and deuteromycota fungi.

The techniques of the invention may be used to treat or/and prevent parasite-caused debilitating human medical conditions arising, for example, from: (i) endoparasites including the plant group of rafflesiaceae, (ii) parasitic worms including the groups of cestodes, nematodes, and trematodes, (iii) ectoparasites including the plant groups of broomrape, cuscuta, mistletoe, santalum, toothwort, and wood rose, (iv) protists in the group of bikonts including apusozoa, archaeplastida, excavata, centrohelida, chromalveolata, and rhizaria, (v) protists in the group of unikonta including amoebozoa and opisthokonta, and (vi) the metazoa group including eumetazoa, placozoa, and porifera.

The techniques of the invention may be used to treat or/and prevent non-pathogenic inflammatory caused debilitating human medical conditions arising, for example, from chronic fibrinous, granulomatous, pseudomembranous, purulent, serous inflammation, or/and ulcerative inflammation. Various changes and applications may thus be made without departing from the true scope of the invention as defined in the appended claims.

We claim:

1. A method comprising administering a medicinal drug to a person sufficiently to treat allergic rhinitis contracted by the person, the medicinal drug formed at least partially with salt of peroxymonosulfuric acid.

2. A method as in claim 1 wherein the salt of peroxymonosulfuric acid comprises at least one of alkali metal salt, alkaline-earth metal salt, and ammonium salt.

3. A method as in claim 1 wherein the administering act comprises administering the medicinal drug topically, orally, intranasally, intraotically, rectally, urethrally, or/and by injection.

4. A method as in claim 1 further including providing the medicinal drug in solid, semiliquid, or/and liquid form.

5. A method as in claim 1 further including providing the medicinal drug in injection form, tablet form, or/and metered-release form.

6. A method comprising administering a medicinal drug to a person sufficiently to treat hemorrhoids contracted by the person, the medicinal drug formed at least partially with salt of peroxymonosulfuric acid.

7. A method as in claim 6 wherein the salt of peroxymonosulfuric acid comprises at least one of alkali metal salt, alkaline-earth metal salt, and ammonium salt.

8. A method as in claim 6 wherein the administering act comprises administering the medicinal drug topically, orally, intranasally, intraotically, rectally, urethrally, or/and by injection.

9. A method as in claim 6 further including providing the medicinal drug in solid, semiliquid, or/and liquid form.

10. A method as in claim 6 further including providing the medicinal drug in injection form, tablet form, or/and metered-release form.

11. A method comprising administering a medicinal drug to a person sufficiently to treat toothache contracted by the person, the medicinal drug formed at least partially with salt of peroxymonosulfuric acid.

12. A method as in claim 11 wherein the salt of peroxymonosulfuric acid comprises at least one of alkali metal salt, alkaline-earth metal salt, and ammonium salt.

13. A method as in claim 11 wherein the administering act comprises administering the medicinal drug topically, orally, intranasally, intraotically, rectally, urethrally, or/and by injection.

14. A method as in claim 11 further including providing the medicinal drug in solid, semiliquid, or/and liquid form.

15. A method as in claim 11 further including providing the medicinal drug in injection form, tablet form, or/and metered-release form.

16. A method comprising administering a medicinal drug to a person sufficiently to treat bromhidrosis contracted by the person, the medicinal drug formed at least partially with salt of peroxymonosulfuric acid.

17. A method as in claim 16 wherein the salt of peroxymonosulfuric acid comprises at least one of alkali metal salt, alkaline-earth metal salt, and ammonium salt.

18. A method as in claim 16 wherein the administering act comprises administering the medicinal drug topically, orally, intranasally, intraotically, rectally, urethrally, or/and by injection.

19. A method as in claim 16 further including providing the medicinal drug in solid, semiliquid, or/and liquid form.

20. A method as in claim 16 further including providing the medicinal drug in injection form, tablet form, or/and metered-release form.

21. A method comprising administering a medicinal drug to a person sufficiently to treat allergic rhinitis contracted by the person, the medicinal drug formed at least partially with potassium hydrogen peroxymonosulfate.

22. A method as in claim 21 further including providing the potassium hydrogen peroxymonosulfate at least partially as a component of a multiple salt com position.

23. A method as in claim 21 wherein the administering act comprises administering the medicinal drug topically, orally, intranasally, intraotically, rectally, urethrally, or/and by injection.

24. A method as in claim 21 further including providing the medicinal drug in solid, semiliquid, or/and liquid form.

25. A method as in claim 21 further including providing the medicinal drug in injection form, tablet form, or/and metered-release form.

26. A method comprising administering a medicinal drug to a person sufficiently to treat hemorrhoids contracted by the person, the medicinal drug formed at least partially with potassium hydrogen peroxymonosulfate.

27. A method as in claim 26 further including providing the potassium hydrogen peroxymonosulfate at least partially as a component of a multiple salt composition.

28. A method as in claim 26 wherein the administering act comprises administering the medicinal drug topically, orally, intranasally, intraotically, rectally, urethrally, or/and by injection.

29. A method as in claim 26 further including providing the medicinal drug in solid, semiliquid, or/and liquid form.

30. A method as in claim 26 further including providing the medicinal drug in injection form, tablet form, or/and metered-release form.

31. A method comprising administering a medicinal drug to a person sufficiently to treat toothache contracted by the person, the medicinal drug formed at least partially with potassium hydrogen peroxymonosulfate.

32. A method as in claim 31 further including providing the potassium hydrogen peroxymonosulfate at least partially as a component of a multiple salt com position.

33. A method as in claim 31 wherein the administering act comprises administering the medicinal drug topically, orally, intranasally, intraotically, rectally, urethrally, or/and by injection.

34. A method as in claim 31 further including providing the medicinal drug in solid, semiliquid, or/and liquid form.

35. A method as in claim 31 further including providing the medicinal drug in injection form, tablet form, or/and metered-release form.

36. A method comprising administering a medicinal drug to a person sufficiently to treat bromhidrosis contracted by the person, the medicinal drug formed at least partially with potassium hydrogen peroxymonosulfate.

37. A method as in claim 36 further including providing the potassium hydrogen peroxymonosulfate at least partially as a component of a multiple salt composition.

38. A method as in claim 36 wherein the administering act comprises administering the medicinal drug topically, orally, intranasally, intraotically, rectally, urethrally, or/and by injection.

39. A method as in claim 36 further including providing the medicinal drug in solid, semiliquid, or/and liquid form.

40. A method as in claim 36 further including providing the medicinal drug in injection form, tablet form, or/and metered-release form.

41. A method comprising administering a medicinal drug to a person sufficiently to treat allergic rhinitis contracted by the person, the medicinal drug formed at least partially with a potassium monopersulfate triple salt composition.

42. A method as in claim 41 wherein the potassium monopersulfate triple salt composition is chemically representable as $(KHSO_5)_x(KHSO_4)_y(K_2SO_4)_z$ where x+y+z are mole fractions whose sum equals 1 and wherein x is 0.43-0.64, y is 0.15-0.43, and z is 0.15-0.43.

43. A method as in claim 41 wherein x is 0.46-0.64, y is 0.15-0.37, and z is 0.15-0.37.

44. A method as in claim 41 wherein the administering act comprises administering the medicinal drug topically, orally, intranasally, intraotically, rectally, urethrally, or/and by injection.

45. A method comprising administering a medicinal drug to a person sufficiently to treat hemorrhoids contracted by the person, the medicinal drug formed at least partially with a potassium monopersulfate triple salt composition.

46. A method as in claim 45 wherein the potassium monopersulfate triple salt composition is chemically representable as $(KHSO_5)_x(KHSO_4)_y(K_2SO_4)_z$ where x+y+z are mole fractions whose sum equals 1 and wherein x is 0.43-0.64, y is 0.15-0.43, and z is 0.15-0.43.

47. A method as in claim 45 wherein x is 0.46-0.64, y is 0.15-0.37, and z is 0.15-0.37.

48. A method as in claim 45 wherein the administering act comprises administering the medicinal drug topically, orally, intranasally, intraotically, rectally, urethrally, or/and by injection.

49. A method comprising administering a medicinal drug to a person sufficiently to treat toothache contracted by the person, the medicinal drug formed at least partially with a potassium monopersulfate triple salt composition.

50. A method as in claim 49 wherein the potassium monopersulfate triple salt composition is chemically representable as $(KHSO_5)_x(KHSO_4)_y(K_2SO_4)_z$ where x+y+z are mole fractions whose sum equals 1 and wherein x is 0.43-0.64, y is 0.15-0.43, and z is 0.15-0.43.

51. A method as in claim 49 wherein x is 0.46-0.64, y is 0.15-0.37, and z is 0.15-0.37.

52. A method as in claim 49 wherein the administering act comprises administering the medicinal drug topically, orally, intranasally, intraotically, rectally, urethrally, or/and by injection.

53. A method comprising administering a medicinal drug to a person sufficiently to treat bromhidrosis contracted by the person, the medicinal drug formed at least partially with a potassium monopersulfate triple salt composition.

54. A method as in claim 53 wherein the potassium monopersulfate triple salt composition is chemically representable as $(KHSO_5)_x(KHSO_4)_y(K_2SO_4)_z$ where x+y+z are mole fractions whose sum equals 1 and wherein x is 0.43-0.64, y is 0.15-0.43, and z is 0.15-0.43.

55. A method as in claim 53 wherein x is 0.46-0.64, y is 0.15-0.37, and z is 0.15-0.37.

56. A method as in claim 53 wherein the administering act comprises administering the medicinal drug topically, orally, intranasally, intraotically, rectally, urethrally, or/and by injection.

57. A method comprising administering a medicinal drug to a person sufficiently to treat urticaria contracted by the person, the medicinal drug formed at least partially with salt of peroxymonosulfuric acid.

58. A method as in claim 57 wherein the administering act comprises administering the medicinal drug topically or/and orally.

59. A method as in claim 57 wherein the salt of peroxymonosulfuric acid comprises at least one of alkali metal salt, alkaline-earth metal salt, and ammonium salt.

60. A method as in claim 57 the salt of peroxymonosulfuric acid comprises potassium hydrogen peroxymonosulfate.

61. A method as in claim 60 further including providing the potassium hydrogen peroxymonosulfate at least partially as a component of a multiple salt composition.

62. A method as in claim 61 wherein the multiple salt composition comprises potassium monopersulfate triple salt composition.

63. A method as in claim 62 wherein the potassium monopersulfate triple salt composition is chemically representable as $(KHSO_5)_x(KHSO_4)_y(K_2SO_4)_z$ where x+y+z are mole fractions whose sum equals 1 and wherein x is 0.43-0.64, y is 0.15-0.43, and z is 0.15-0.43.

64. A method as in claim 63 wherein x is 0.46-0.64, y is 0.15-0.37, and z is 0.15-0.37.

* * * * *